(12) United States Patent
Lee et al.

(10) Patent No.: US 10,151,753 B2
(45) Date of Patent: Dec. 11, 2018

(54) MICROFLUIDIC DEVICES FOR ISOLATING PARTICLES

(71) Applicant: The General Hospital Corporation, Boston, MA (US)

(72) Inventors: Hakho Lee, Acton, MA (US); Ralph Weissleder, Peabody, MA (US); Kyungheon Lee, Cambridge, MA (US); Jun Song, Somerville, MA (US)

(73) Assignee: The General Hospital Corporation, Boston, MA (US)

( * ) Notice: Subject to any disclaimer, the term of this patent is extended or adjusted under 35 U.S.C. 154(b) by 39 days.

(21) Appl. No.: 15/104,775

(22) PCT Filed: Dec. 17, 2014

(86) PCT No.: PCT/US2014/070956
§ 371 (c)(1),
(2) Date: Jun. 15, 2016

(87) PCT Pub. No.: WO2015/095395
PCT Pub. Date: Jun. 25, 2015

(65) Prior Publication Data
US 2016/0313332 A1 Oct. 27, 2016

Related U.S. Application Data

(60) Provisional application No. 61/917,268, filed on Dec. 17, 2013.

(51) Int. Cl.
*B01L 3/00* (2006.01)
*G01N 33/574* (2006.01)
(Continued)

(52) U.S. Cl.
CPC ...... *G01N 33/574* (2013.01); *B01L 3/502715* (2013.01); *B01L 3/502761* (2013.01);
(Continued)

(58) Field of Classification Search
None
See application file for complete search history.

(56) References Cited

U.S. PATENT DOCUMENTS 6,007,690 A * 12/1999 Nelson ............. G01N 27/44791
204/450
7,104,659 B2 9/2006 Grier et al.
(Continued)

OTHER PUBLICATIONS

International Search Report and Written Opinion dated Apr. 15, 2015 in International Application No. PCT/US2014/070956, 13 pgs.
(Continued)

*Primary Examiner* — Betty J Forman
(74) *Attorney, Agent, or Firm* — Fish & Richardson P.C.

(57) ABSTRACT

In one aspect, a system for isolating particles includes a first array of magnets, a second array of magnets arranged generally in parallel with and spaced apart from the first array of magnets, and a micro fluidic device. The micro fluidic device includes a substrate, an inlet arranged on the substrate and configured to receive a fluid sample, an outlet arranged on the substrate, a first region of the substrate including a channel connected to the inlet, where the first region of the substrate is arranged to sandwich the channel between the first and second arrays of magnets.

19 Claims, 29 Drawing Sheets

(51) Int. Cl.

| | | |
|---|---|---|
| *B03C 1/033* | (2006.01) | |
| *B03C 1/28* | (2006.01) | |
| *B03C 1/08* | (2006.01) | |
| *B03C 1/30* | (2006.01) | |
| *G01N 1/40* | (2006.01) | |
| *G01N 15/14* | (2006.01) | |
| *G01N 21/64* | (2006.01) | |
| *G01N 33/50* | (2006.01) | |
| *G01N 15/00* | (2006.01) | |
| *G01N 15/10* | (2006.01) | |

(52) U.S. Cl.
CPC ............ *B03C 1/0332* (2013.01); *B03C 1/08* (2013.01); *B03C 1/288* (2013.01); *B03C 1/30* (2013.01); *G01N 1/4077* (2013.01); *G01N 15/1463* (2013.01); *G01N 21/6428* (2013.01); *G01N 33/5008* (2013.01); *G01N 33/5011* (2013.01); *B01L 2200/0647* (2013.01); *B01L 2200/12* (2013.01); *B01L 2300/06* (2013.01); *B01L 2300/0654* (2013.01); *B01L 2300/0848* (2013.01); *B03C 2201/18* (2013.01); *B03C 2201/26* (2013.01); *G01N 2001/4038* (2013.01); *G01N 2015/0065* (2013.01); *G01N 2015/1006* (2013.01)

(56) References Cited

U.S. PATENT DOCUMENTS

| | | | |
|---|---|---|---|
| 7,137,574 B2 | 11/2006 | Grier et al. | |
| 7,285,412 B2 | 10/2007 | Casagrande et al. | |
| 7,759,635 B2 | 7/2010 | Boer et al. | |
| 2002/0063868 A1* | 5/2002 | Florin | G01N 15/1468 356/625 |
| 2003/0022370 A1* | 1/2003 | Casagrande | B01L 3/5085 435/372.1 |
| 2003/0045005 A1* | 3/2003 | Seul | B01J 19/0046 436/523 |
| 2010/0300978 A1* | 12/2010 | Ramadan | B03C 1/0332 210/695 |
| 2011/0137018 A1* | 6/2011 | Chang-Yen | G01N 35/0098 530/412 |
| 2013/0271250 A1 | 10/2013 | Weissleder et al. | |

OTHER PUBLICATIONS

Chung et al., "Rare cell isolation and profiling on a hybrid magnetic/size-sorting chip," Biomicrofluidics, 2013, 7: 054107.

Ding et al., "On-chip manipulation of single microparticles, cells, and organisms using surface acoustic waves," PNAS, 2012, 109: 11105-11109.

International Preliminary Report on Patentability dated Jun. 30, 2016 in International Application No. PCT/US2014/070956, 8 pages.

Li et al., "A simple method for evaluating the trapping performance of acoustic tweezers," Applied physics letters, Feb. 2013, 102: 084102.

Petersen et al., "Ascites analysis by a microfluidic chip allows tumor-cell profiling," PNAS, 2013, 1-9.

* cited by examiner

2100

MICROFLUIDIC DEVICES FOR ISOLATING PARTICLES

RELATED APPLICATIONS

The present application is a 371 application of PCT/US2014/070956, filed Dec. 17, 2014, which claims priority from U.S. Provisional Patent Application Ser. No. 61/917,268, filed Dec. 17, 2013, the subject matter of which are incorporated herein by reference in their entireties.

TECHNICAL FIELD

This disclosure relates to microfluidic devices for isolating particles.

BACKGROUND

Magnetic fields can have broad applications in biotechnology and medicine. For example, systems utilizing magnetic fields can have applications in cancer diagnostics, drug discovery, and stem cell research, among others. One particular area includes magnetic separation of cells, in which cells of interest are attached to magnetic biomarkers in a solution and the solution is then introduced into an area having a magnetic field. The magnetic field serves to isolate and/or filter the cells having the attached biomarkers for subsequent analysis, modification, or use.

SUMMARY

This disclosure describes techniques and systems for utilizing arrays of magnets to isolate target particles (e.g., rare target particles such as rare cells, e.g., circulating tumor cells or fetal cells in maternal blood) from other particles (e.g., other types of cells) in a sample fluid (e.g., biological fluid, such as blood sample). For example, the arrays of magnets can be assembled onto a microfluidic device to generate strong magnetic fields in regions of one or more channels in the microfluidic device. The strong magnetic fields can isolate particles bound to magnetic beads from other particles in the sample fluid. The design and arrangement of the arrays of magnets can efficiently isolate particles while allowing high throughput of sample fluid in the microfluidic device.

In some embodiments, the techniques and systems disclosed herein enable negative and positive selection and separation of particles in a sample fluid as the fluid flows through a microfluidic device by utilizing arrays of magnets and size-based particle capture. For example, the arrays can be arranged as one-dimensional or two-dimensional "checkerboards" of magnets with alternating polarities, as described in further detail below. The arrays of magnets can be used to immuno-magnetically deplete abundant host cells (e.g., leukocytes). Following negative selection, remaining particles (e.g., target cancer cells or fetal cells) that are not immuno-magnetically depleted can be flowed into a particle capture zone for capturing and sorting according to their size. For example, the captured particles can be manipulated using a tweezer device (e.g., optical or acoustic tweezer device) and analyzed in an efficient manner. For example, the captured particles can be analyzed in situ for a comprehensive and multifaceted evaluation, including single cell enumeration and imaging, molecular and genetic profiling, and drug-treatment responses. In particular, a user or automated system can utilize the tweezer device to lift and displace captured particles for analysis.

In one aspect, a system for isolating particles includes a first array of magnets, a second array of magnets arranged generally in parallel with and spaced apart from the first array of magnets, and a microfluidic device. The microfluidic device includes a substrate, an inlet arranged on the substrate and configured to receive a fluid sample, an outlet arranged on the substrate, a first region of the substrate including a channel connected to the inlet, where the first region of the substrate is arranged to sandwich the channel between the first and second arrays of magnets, and a second region of the substrate in fluid communication with the channel and including a particle capture zone containing a plurality of particle capture sites, where each particle capture site including a receptacle sized to confine a first type of particle and an opening in fluid communication with the receptacle, wherein a size of the receptacle is larger than a size of the opening.

Implementations of this aspect may include or more of the following features.

In some implementations, the first array of magnets and the second array of magnets can each include magnets arranged such that adjacent magnets have dipole moments aligned in opposite directions.

In some implementations, the magnets in the first array of magnets and the second array of magnets can each include NdFeB, SmCo, Fe, Ni, Co, FePt, $MnFe_2O_4$, $CoFe_2O_4$, $NiFe_2O_4$, $ZnMnFe_2O_4$, or iron oxide.

In some implementations, a length of at least one of magnets in the first array of magnets along a fluid propagation direction through the channel can be 100 μm or more.

In some implementations, a distance between the first array of magnets and the second array of magnets can be 0.5 mm or more.

In some implementations, a peak magnitude value of a magnetic field strength at a point between the first array of magnets and the second array of magnets can be about 0.45 T or more.

In some implementations, a magnitude of an average magnetic field strength along a line extending from the first array of magnets to the second array of magnets can be about 0.35 T or more.

In some implementations, the system can further include a tweezer device configured to displace the particle captured in one of the particle capture sites. The system can further include a receiver device configured to receive the displaced particle. The tweezer device can be an optical tweezer device. The optical tweezer device can include an optical source for generating an optical beam, and a lens for focusing the optical beam into one of the particle capture sites.

In some implementations, for at least one particle capture site, the receptacle can be sized to receive and confine a single first type of particle, and, for the at least one particle capture site, the opening can be small enough to prohibit passage of the first type of particle and large enough to allow passage of a second type of particle.

In some implementations, at least one particular capture site can include a first wall and a corresponding second wall, where the receptacle bounded by the first and second wall, and where the opening is defined between an end of the first wall and an end of the second wall.

In some implementations, at least one of the particle capture sites can include a wall, where the receptacle is defined by a recess in the wall, and wherein the opening extends from the receptacle on a first side of the wall to a second opposite side of the wall.

In some implementations, during operation of the system the receptacle and opening of each particle capture site can be aligned substantially parallel to a direction of fluid flow in the second region.

In some implementations, the particle capture sites can be arranged in at least two rows, where the particle capture sites in each row are spatially offset from the particle capture sites in an adjacent row in two orthogonal directions.

In some implementations, the system can further include at least one additional inlet in fluid communication with the second region, where the additional inlet is arranged to receive one or more additional fluid samples and output the one or more additional fluid samples through at least the second region.

In some implementations, the system can further include a fluid manifold arranged on the substrate between the particle capture zone and the outlet.

In another aspect, a method for isolating particles includes providing a first and a second array of magnets, where the first and second arrays of magnets are positioned to sandwich a region including a channel of a microfluidic device. The method also includes providing a sample fluid comprising a plurality of particles into the channel, where at least one first type of particle is bound to a magnetic bead, and where a magnetic field extending between the first and second magnet arrays within the channel causes the at least one first type of particle to separate from remaining particles in the fluid sample. The method also includes providing the fluid sample containing the remaining particles to a particle capture zone of the microfluidic device, where the particle capture zone comprises a plurality of particle capture sites. The method also includes capturing one or more second type of particles at the particle capture sites of the microfluidic device, where the one or more second type of particles are not bound to a magnetic bead. Each particle capture site includes a receptacle sized to confine the second type of particle and an opening in fluid communication with the receptacle, and where a size of the receptacle is larger than a size of the opening.

Implementations of this aspect may include or more of the following features.

In some implementations, capturing the second type of particle can include receiving a single second type of particle in a receptacle of one of the particle capture sites.

In some implementations, the method can further include displacing the one or more second type of particles from the particle capture sites using an optical tweezer. Displacing the one or more second type of particles from the particle capture sites can include displacing a single one of the second type of particles from a single one of the particle capture sites. The optical tweezer can be configured to provide a plurality of optical traps.

In some implementations, the method can further include collecting the displaced second type of particle in a receiver device.

In some implementations, the method can further include flowing a first additional fluid through at least the particle capture zone. The first additional fluid can include a plurality of first fluorescent markers, and the method can further include allowing the plurality of the first fluorescent markers to bind to one or more of the second type of particle. The method can further include optically exciting the first fluorescent markers bound to the one or more second type of particle, obtaining an image of the one or more second type of particle, and determining a characteristic of the second type of particle based on the obtained image. The characteristic can include a presence or absence of a first biomarker expressed by the second type of particle. Determining the characteristic of the second type of particle based on the obtained image can include determining an intensity of fluorescence associated with the second type of particle based on the obtained image.

In some implementations, the method can further include flowing an elutant through at least the particle capture zone, where flowing the elutant causes the fluorescently labeled particles to release from second type of particle. The method can further include flowing a second additional fluid sample through at least the particle capture zone, where the second additional fluid includes a plurality of a second type of fluorescent marker, and where one of more of the second type of fluorescent markers bind to one or more of the second type of particle.

In some implementations, the method can further include optically exciting one or more of the second fluorescent markers bound to second type of particle, obtaining a second image of the second type of particle, and determining a characteristic of the second type of particle based on the obtained second image. The characteristic can include a presence or absence of a second biomarker expressed by the second type of particle different than the first biomarker. Determining the characteristic of the second type of particle based on the obtained second image can include determining an intensity of fluorescence associated with the second type of particle based on the obtained second image.

In some implementations, the first additional fluid substance can include a drug such that the second type of particle is exposed to the drug. A concentration of the drug within the additional fluid can be graded.

In some implementations, the method can further include culturing the at least one second type of particle in the particle capture zone after the at least one second type of particle is captured.

The techniques and systems disclosed in this specification provide numerous benefits and advantages (some of which can be achieved only in some of the various aspect and implementations) including the following. The disclosed systems can be assembled as modular components, which can lead to ease and cost effective manufacturing. For example, manufacturing of separate modular components can be easier and less expensive than fabricating an integrated system. Moreover, the approach using modular components can allow a user to easily replace different sample fluids, magnets, channel types so as to increase throughput of the analysis while maintaining a sealed system without fluid leakage. The systems can include magnetically detachable fluidic ports, which can significantly simplify the fluidic connection to microfluidic devices.

In general, the disclosed techniques can be used to combine both negative and the positive selection of particles (e.g., negative and positive cell enrichment), thereby enabling high throughput and non-biased isolation of target particles. Arrays of magnets can be used to generate a strong magnetic force with a relatively long range, and thereby allowing efficient isolation of particles attached to magnetic beads. Furthermore, because the magnetic force can be long range, the arrays of magnets can be placed outside a microfluidic device so that the magnets do not contact the sample fluid. Thus, contamination of the magnets can be avoided, and the magnets may easily be reused for testing of different sample fluids.

In general, the disclosed techniques can be used to provide systems with particle capture sites with a hydrodynamic design to ensure a single-cell trapping per site, while minimizing the risk of clogging the microfluidic devices. The particle capture sites can be further laid out into a size-gradient array, so as to differentially capture particles based on their size. Furthermore, the systems can include a tweezer device to manipulate particles captured in particle capture sites. For example, the tweezer device can be used to manipulate and retrieve captured cells at a single-cell resolution. This capability, combined with emerging molecular techniques, can enable the study of single-cell genomics and proteomics.

In general, the disclosed techniques also enable analysis of individual rare cells through the combination of magnetic depletion of large quantities of undesired cells and capture sites configured to receive and trap individual rare cells. The capture sites have the further advantage of being able to provide additional filtering so that only rare cells are trapped and analyzed.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present implementations, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages will be apparent from the following detailed description, and from the claims.

BRIEF DESCRIPTION OF THE DRAWINGS

FIGS. 18A-C are images showing a particle capture site in a microfluidic device with an optical trap.

DETAILED DESCRIPTION

Figure 1:
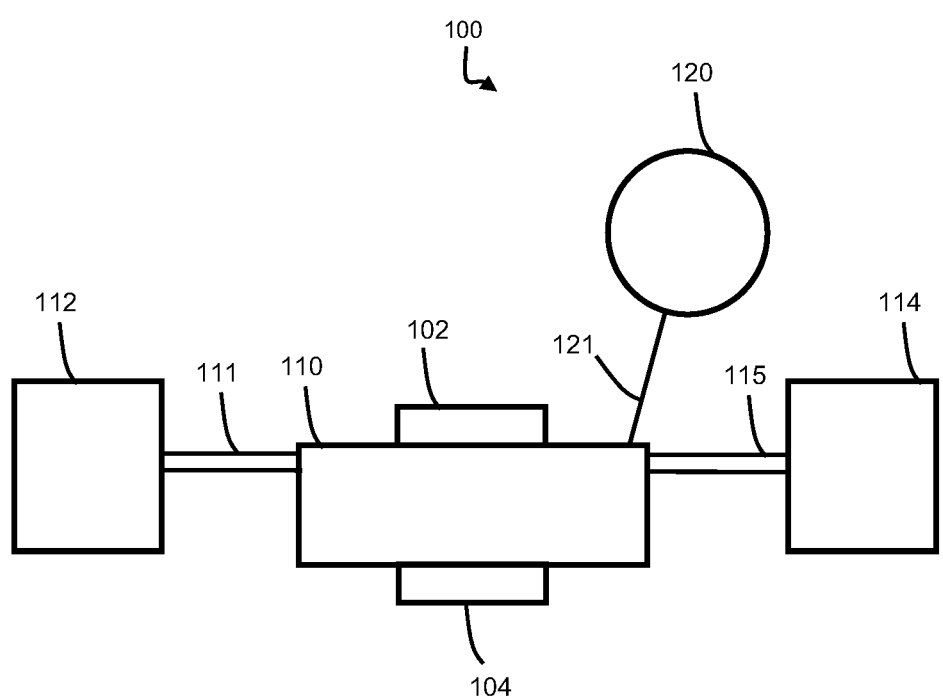
FIG. 1 is a schematic diagram showing a system for isolating particles.

The methods and systems described herein can be implemented in many ways. Some useful implementations are described below. The scope of the present disclosure is not limited to the detailed implementations described in this section, but is described in broader terms in the claims.

Introduction

Various particles (e.g., tumor cells) are important biomarkers for clinical practice as well as fundamental research. For example, circulating tumor cells ("CTCs"), which are shed from primary tumors, can be a harbinger of tumor expansion. Proteomic characterization of proliferative markers such as Ki-67 and hormonal markers such as androgen receptor in prostate cancer can be predictive of treatment outcomes. To detect and characterize particles such as tumor cells and other biomarkers, a user often flows a sample fluid (e.g., a biological fluid such as a blood, e.g., whole blood or buffy coat, lymph, cerebrospinal fluid, urine, saliva, or a sputum sample) through channels of a microfluidic device to separate different types of particles. Subsequent characterization is based on the separation of particles. However, routine detection and characterization of particles in the sample fluid typically require screening a large number of particles and enrichment of heterogeneous targets to obtain accurate results.

Accordingly, the techniques described herein provide systems that can be used to isolate target particles with high enrichment while reducing the probability of missing the detection of a rare target particle in a given sample fluid. For example, the systems can utilize arrays of magnets sandwiching regions of channels of the microfluidic device, through which the sample fluid flows. In such regions of the channels, the design and arrangement of the arrays of magnets can provide strong magnetic forces onto particles bound to magnetic beads so that such particles are attracted towards the magnets, and thereby isolating the attracted particles from remaining particles in the sample fluid. For example, abundant host particles (e.g., blood cells) can be magnetically depleted in this manner so that target cells that are not magnetically depleted can be enriched with high efficiency and throughput. Moreover, the disclosed arrangements of magnet arrays can provide a stronger magnetic force than the case in which magnets are positioned on only one side of the channels.

Moreover, the microfluidic devices can include a particle capture zone containing particle capture sites. These sites can be used to capture particles with specific sizes among the remaining particles. For example, the size and shape of different sites can be designed to capture specific particles while allowing other particles to pass through. In this approach, the microfluidic devices can provide positive selection of particles along with a size sorting capability.

Both negative and positive selection can be enabled by a single microfluidic device. Thus, the microfluidic device can provide high throughput of separating particles so that a user may carry out tests easily in a fast manner, which may allow ease of repeated measurements as well as operation of different types of measurements. Detailed embodiments and various advantages are described in the following.

General Systems

FIG. 1 is a schematic diagram showing a system 100 for isolating particles. System 100 can include an array of magnets 102 and an array of magnets 104 sandwiching a region of a microfluidic device 110 so as to provide magnetic fields in the region. The microfluidic device 110 can be coupled to a sample fluid provider 112 so that the microfluidic device 100 can receive sample fluid from the sample provider 112. In some embodiments, coupling 111 can be a tube connecting the sample fluid provider 112 to an inlet (not shown) of the microfluidic device 110. The sample fluid received through the inlet can flow through channels (not shown) of the microfluidic device towards an outlet (not shown) of the microfluidic device 100. During the flow, the magnetic fields provided by the arrays of magnets 102 and 104 isolate particles bounded with magnetic beads. Thus, particles bounded to magnetic beads become attached to walls of the channels by the magnetic forces and such particles are thus separated from other particles in the sample fluid. On the other hand, particles that are not attracted by the magnetic forces can flow towards the outlet.

As described later in detail, the microfluidic device 110 can include a particle capture zone for capturing particles in the sample fluid. The system 100 can include a tweezer (e.g., optical tweezer, acoustic tweezer) device 120 coupled to the microfluidic device 110 through coupling 121. In some embodiments, the coupling 121 can be an optical beam used to trap particles captured in the particle capture zone. For example, the tweezer device 110 can lift and move a specific captured particle (selected either by an operator of the system who visualizes the particles on a monitor, or by a system that automatically targets specific particles, e.g., based on a fluorescent or other reporter group). When the specific captured particle is lifted and the tweezer device 120 releases the lifted particle, fluid flow can transport the lifted particle towards the outlet.

The outlet of the microfluidic device 110 can be coupled to a receiver device 114. In some embodiments, coupling 115 can be a tube connecting the outlet of the microfluidic device 110 to the receiver device 114. The receiver device 114 can have multiple containers for containing selected particles or fluids. For example, in one container, the receiver device 114 can contain particles that are not isolated by the magnetic forces or captured in the particle capture zone. In another container, the receiver device 114 can contain selected particles that are specifically released by the tweezer device 120 and transported to the outlet.

Figure 2:
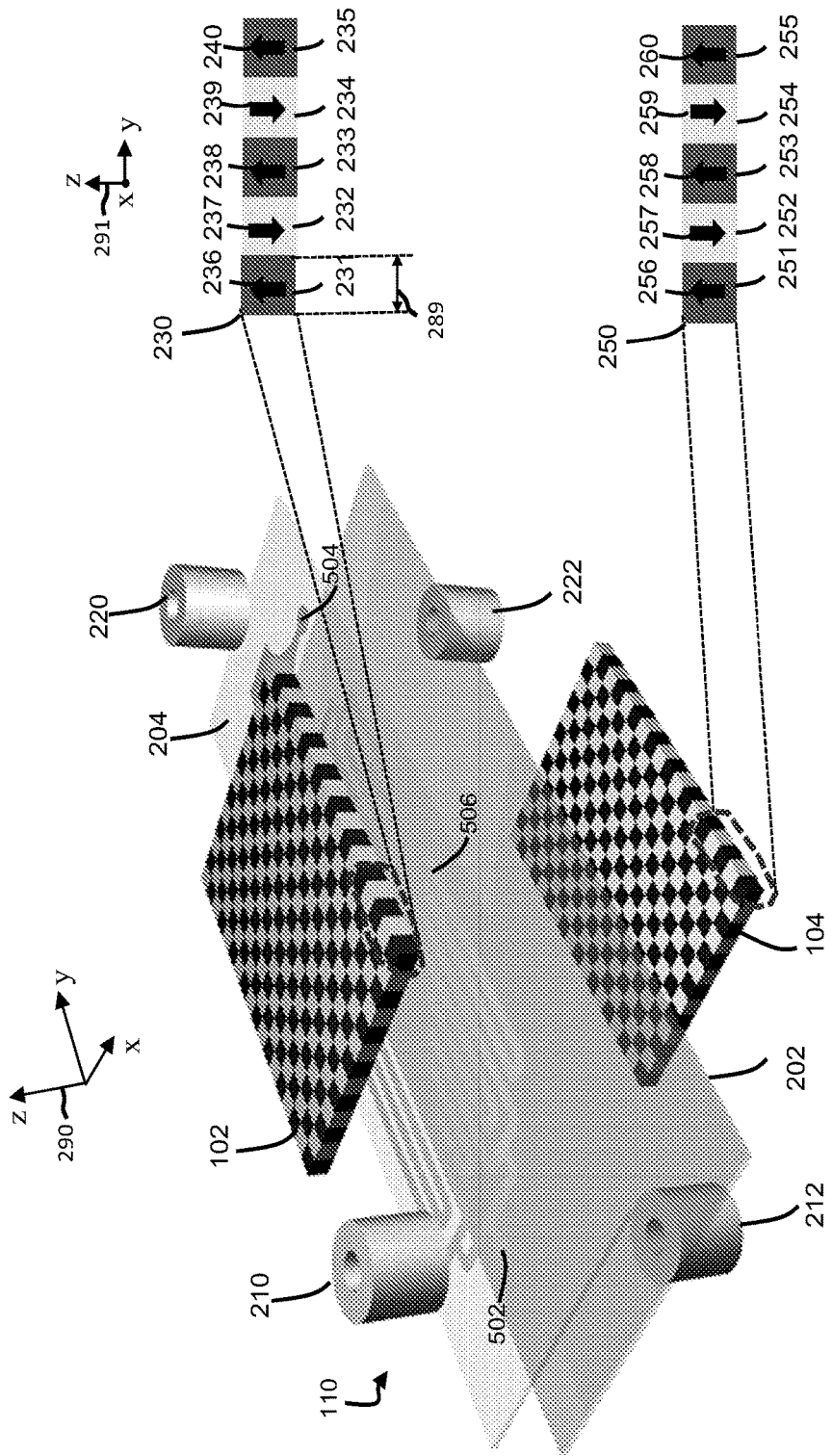
FIG. 2 is a schematic diagram showing a portion of the system described in FIG. 1.

FIG. 2 is a schematic diagram showing a portion of the system 100 described in FIG. 1. Separations between various elements are depicted schematically for illustrative purposes. Global coordinate 290 indicates the orientation of the schematic drawing. In this example, the microfluidic device 110 has a substrate, which includes a microfluidic channel layer 204 and a plate 202. The plate 202 supports the microfluidic channel layer 204. In some embodiments, the plate 202 can include glass, microslide, or plastic material. The plate 202 can be transparent to visible light for imaging or optical manipulation purposes. The microfluidic channel layer 204 can include a polydimethylsiloxane (PDMS), glass, or plastic layer. In certain embodiments, either of the microfluidic channel layer 204 and plate 202 can be a plastic mold configured to hold either or both of the arrays of magnets 102 and 104.

The microfluidic channel layer 204 can include inlet 502, channel 506, particle capture zone 508, fluid manifold 505 and outlet 504, which will be described later. In this example, another plate (not shown) is positioned between the array of magnets 102 and the microfluidic channel 204. Such configuration is described later in relation to FIG. 4. In some embodiments, either of the arrays of magnets 102 or 104 can be directly in contact with the microfluidic channel 204 without a plate in between. The channel 506 can be embedded within microfluidic channel layer 204 so that top and bottom surfaces of the microfluidic channel layer 204 is in contact with either the arrays of magnets 102 and 104 and the plates, respectively. In certain embodiments, channel 506 can be open on one side of the microfluidic channel layer 204 so that channels are open facing towards the plate 202. Thus, the plate 202 can act as a sealing layer for the channels in the microfluidic channel layer 204.

In some embodiments, the system 100 can include detachable inlet elements 210 and 212. For example, the detachable inlet elements 210 and 212 can be cylindrical magnets with a fluidic port of a hollow bore. The inlet elements 210 and 212 can clamp and hold the microfluidic channel layer 204 and the plate 202. In this case, the inlet elements 210 and 212 can clamp and seal the microfluidic device 110 with mitigated effects of stress applied to the microfluidic device 110 due to clamping. The inlet elements 210 and 212 can also allow connection of tubes to the sample provider 112. In certain embodiments, the inlet elements 210 and 212 can function as a stand-alone reservoir of sample fluid. Because the magnetic force between the inlet elements 210 and 212 can tightly clamp the microfluidic device 110, the inlet elements 210 and 212 can effectively seal the tube connection between the sample provider 112 and the microfluidic device 110 without fluid leakage. On the other hand, a user may easily remove the inlet elements 210 and 212, for example, in a direction orthogonal to the magnetic forces between the inlet elements 210 and 212. Thus, the user may easily replace one microfluidic device from another without issues of fluid leakage.

The system 100 can include detachable outlet elements 220 and 222. Similarly, as described in relation to inlet elements 210 and 212, the outlet elements 220 and 222 can be magnetic and be used to clamp the microfluidic device 110 for sealing while allow easy replacement of the microfluidic device.

In certain embodiments, either of the detachable inlet and outlet elements 210, 212, 220 and 222 can be screwed onto the microfluidic device 110. This approach can provide a tight seal between the microfluidic device 110, sample provider 112, and receiver device 114.

In some embodiments, the microfluidic device 110 can include another plate (not shown) between the microfluidic channel layer 204 and the array of magnets 102. In this approach, the microfluidic channel layer 204 is sandwiched between the plate 202 and another plate, which can lead to uniform pressure being applied over the microfluidic channel layer 204.

The array of magnets 102 is positioned adjacent to the microfluidic device 110 in the positive z-direction. The array of magnets 104 is positioned adjacent to the microfluidic device 110 in the negative z-direction. Thus, in this example, the arrays of magnets 102 and 104 sandwich and provide magnetic fields in a region of the microfluidic device 110. The magnetic attraction between the arrays of magnets 102 and 104 can clamp the microfluidic device 110 so as to provide a tight seal without leakage. In certain embodiments, either of the arrays of magnets 102 and 104 can be fixed in a molding of the microfluidic device 110 so that either of the arrays can hold onto the microfluidic device 110 without the presence of the other array.

Moreover, magnetic dipole moments of the magnets in the arrays of magnets 102 and 104 are arranged to provide a strong magnetic field strength and large magnetic field gradient in the region of the one or more channels in the microfluidic device 110. Orientations of the magnetic dipole moments of the magnets are described below.

Referring back to FIG. 2, a zoomed view depicts a 1-dimensional (1D) subset array 230 of the array of magnets 102 including five magnets 231-235. Another zoomed view depicts a 1D subset array 250 of the array of magnets 104 including five magnets 251-255. Only five magnets are described for illustrative purposes according to global coordinate 291.

In this disclosure, two magnets being "directly adjacent" to one another means that the two magnets are positioned next to one another without another magnet in between. In this example, the magnet 231 has a magnetic dipole moment 236 pointing in the z-direction. Magnet 232, which is directly adjacent to magnet 231, has a magnetic dipole moment 237 pointing in the negative z-direction. Magnet 233, which is directly adjacent to magnet 232 and 234, has a magnetic dipole moment 238 pointing in the positive z-direction. Magnet 234 has its magnetic dipole moment 239 pointing in the negative z-direction, and magnet 235 has its magnetic dipole moment 240 pointing in the positive z-direction.

Furthermore, magnets 251, 253 and 255 of subset array 250 have their respective magnetic dipole moments 256, 258 and 260 pointing in the positive z-direction. Magnets 252 and 254 have their respective magnetic dipole moments 257 and 259 pointing in the negative z-direction.

Generally, each of the arrays of magnets 102 and 104 can include a number of magnets to cover the area of channels 506 in the microfluidic device 110. For example, the array of magnets 102 can include 5 or more (e.g., 10 or more, 30 or more, 50 or more, 100 or more, 500 or more) rows. Each row of the array of magnets 102 can include 5 or more (e.g., 10 or more, 30 or more, 50 or more, 100 or more, 500 or more) magnets. In some embodiments, a length of the whole array of magnets 102 can be 30 mm or more (e.g., 40 mm or more, 50 mm or more).

In the example shown in FIG. 2, magnet 231 has a length 289 of 1 mm. In some embodiments, the length 289 can be 0.1 mm or more (e.g., 0.3 mm or more, 0.5 mm or more, 1.5 mm or more, 2 mm or more, 3 mm or more). In some cases, the length 289 can be between 0.1 mm and 10 mm (e.g., between 0.1 mm and 1 mm, between 1 mm and 2 mm, between 2 mm and 3 mm, between 3 mm and 4 mm, between 4 mm and 5 mm, or between 5 mm and 10 mm). The other magnets can have the same length as length 289. In certain embodiments, the length 289 can have a maximum length of about 5 mm or less (e.g., 4 mm or less, 3 mm or less). Generally, different magnets can have the same or different lengths and the magnets can be arranged to provide a desired magnetic field distribution according to the design of channel 506.

It is understood that the array of magnets 104 can have similar characteristics described in relation to the array of magnets 102 described in the preceding paragraphs.

The individual magnets can be permanent magnets. In some embodiments, the magnets can comprise a magnetic material including NdFeB, SmCo, Fe, Ni, Co, FePt, $MnFe_2O_4$, $CoFe_2O_4$, $NiFe_2O_4$, $ZnMnFe_2O_4$, or iron oxide. The magnetic material can be selected to have a high magnetic permeability for providing strong magnetic fields.

Figure 3:
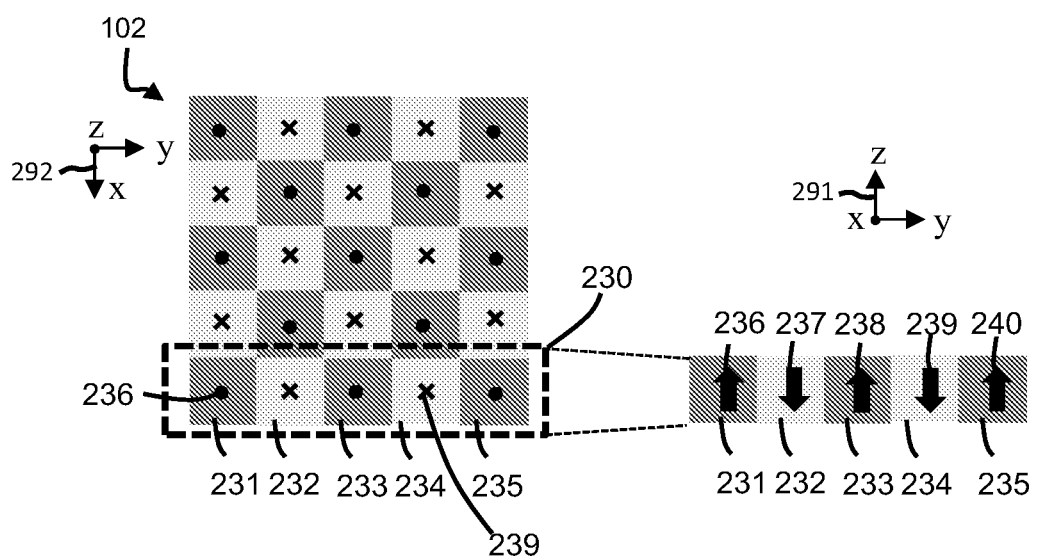
FIG. 3 is a schematic diagram showing a portion of an array of magnets.

FIG. 3 is a schematic diagram showing a portion of the array of magnets 102 in a different perspective according to global coordinate 292. In this disclosure, the "dot" notation refers to a direction pointing out of the drawing plane, and the "cross" notation refers to a direction pointing into the drawing plane. Accordingly, FIG. 3 depicts magnet 231 with its magnetic dipole moment 236 pointing in the positive z-direction and magnet 234 with its magnetic dipole moment 239 pointing in the negative z-direction. As mentioned earlier, magnet 232, which is directly adjacent to magnets 231 and 233, has its magnetic dipole moment 237 pointing in the negative z-direction. Thus, in the example shown in FIG. 3, magnets directly adjacent one another have magnetic dipole moments pointing in different direction. Further, FIG. 3 depicts the orientation of magnetic dipole moments of the magnets arranged in a 2D array in a plane parallel to the x- and y-direction. It is understood that the magnetic dipole moments of the magnets are arranged in an alternating manner, such that adjacent magnets have dipole moments aligned in opposite directions. Such a configuration of array of magnets 102 described in relation to FIG. 3 may also be referred as a "checkerboard" pattern.

The arrays of magnets 104 lie below the arrays of magnets 102 in the negative z-direction, as shown in FIG. 2. As similarly described in relation to FIG. 3, subset array 250 includes magnets 251-255 which have magnetic dipole moments 256-260, respectively, pointing in different directions for directly adjacent magnets. It is understood that the magnetic dipole moments of the magnets are arranged in an alternating manner.

Referring back to FIG. 2, the array of magnets 102 lie in a first plane parallel to the x-y plane. The array of magnets 104 lie in a second plane parallel to the x-y plane. Hence, in this example, the first and second planes are parallel to each another. In some embodiments, the first and second planes are substantially parallel to each another within 10° (e.g., within 5°, within 3°, within 1°).

The arrays of magnets 102 and 104 are arranged to sandwich the microfluidic device 110. Thus, the array of magnets 102 is displaced relative to the array of magnets 104 in the positive z-direction, which are generally parallel to each other in some embodiments. In other embodiments, the two arrays may be arranged at an angle, e.g., a slight angle, to each other. The relative positions between individual magnets of the arrays of magnets 102 and 104 are described in comparison to subset arrays 230 and 250 in FIG. 2. The magnet 231 is positioned relative to magnet 251 in the positive z-direction, and magnet 232 is positioned relative to magnet 242 in the positive z-direction. Similarly, magnets 233-235 are positioned relative to magnets 253-255 in the positive z-direction. Generally, magnets of the array of magnets 102 are positive relative to magnets in the array of magnets 104 in the positive z-direction so that magnets with magnetic dipole moments point in the same direction are aligned to one another. For example, magnetic dipole moment 236 is aligned to its corresponding magnetic dipole moment 256, and the magnetic dipole moment 237 is aligned to its corresponding magnetic dipole moment 257. In certain embodiments, at least some of the magnetic dipole moments and corresponding magnetic dipole moments can point substantially in the same direction. For example, at least some of the magnetic dipole moments and corresponding magnetic dipole moments point in the same direction within 1° or less (e.g., 2° or less, 5° or less, 10° or less).

Figure 4:
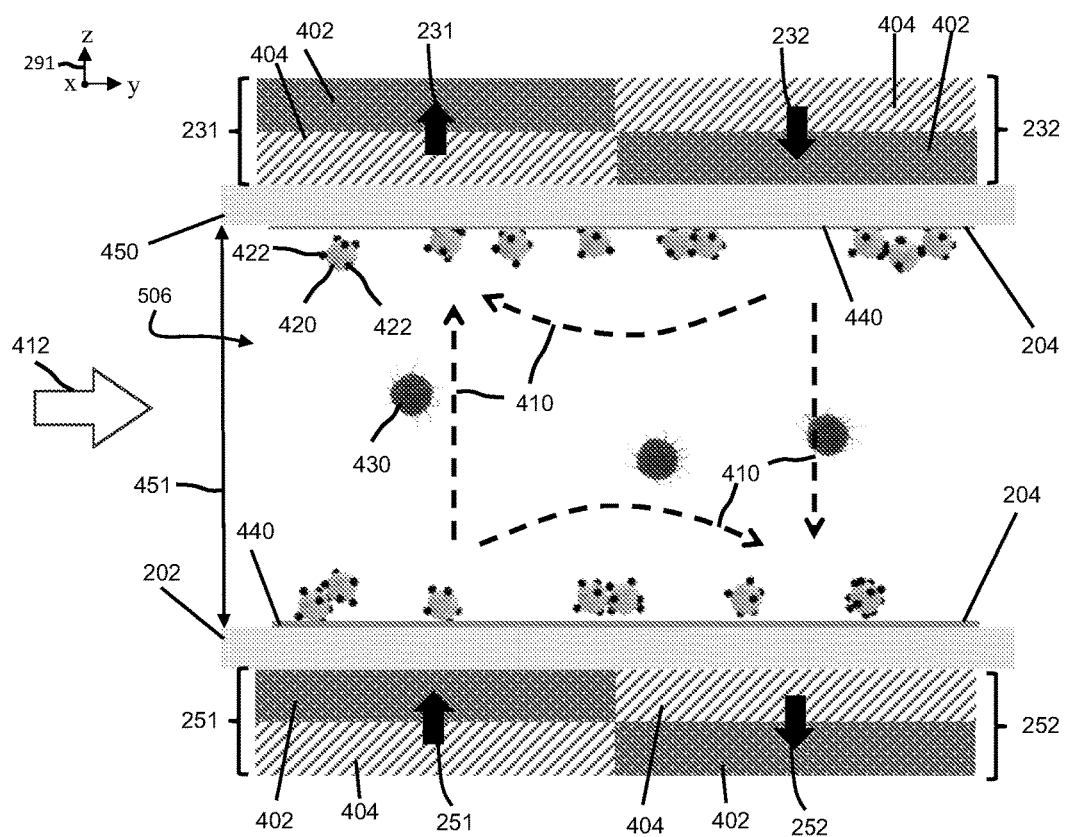
FIG. 4 is a schematic diagram showing a portion of a cross-section of the system described in relation to FIG. 2.

To further illustrate the arrangement of the arrays of magnets 102 and 104, FIG. 4 is a schematic diagram showing a portion of a cross-section of the system 100 described in relation to FIG. 2. Global coordinate 291 indicates the perspective of the cross-section. For illustrative purposes, magnets 231, 231, 251 and 252 are depicted with their respective magnetic poles 402 and 404. The magnet 231 is position above the magnet 251 in the positive z-direction, and the magnet 232 is positioned above the magnet 252 in the positive z-direction. As shown, magnetic dipole moments 231 and 251 point in the same direction, and magnetic dipole moments 232 and 252 point in the same direction, opposite of that of magnetic dipole moments 231 and 251. As shown in FIG. 3, alternating arrangement of the magnetic dipole moments extend in both the x- and y-directions. Such a configuration can generate strong magnetic fields 410 and larger magnetic field gradients within channel 506 of the microfluidic device 110.

The alignment of magnetic dipole moments 231 and 251 reinforce the magnetic fields of the magnetic dipole moments 231 and 251 to provide strong magnetic fields. Such magnetic fields at certain locations can be even stronger than that of the case when only one array of magnets exists adjacent to the channel 506. Moreover, the alternating magnetic dipole moments above and below the channels lead to a large gradient of the magnetic fields because the fields bend around between adjacent magnetic dipole moments.

Assuming a spherical shape, a magnetic particle place within a magnetic field distribution can be described to experience a magnetic force $\vec{F}_B$ according to Eq. (1) presented below:

$$\vec{F}_B = \frac{V\chi}{\mu_0}(\vec{B} \cdot \vec{\nabla})\vec{B}. \tag{1}$$

where V is the volume of the particle ($m^3$), $\chi$ is the magnetic susceptibility (unit-less) and $\mu_0$ is the vacuum permeability (V×s/A×m). $\vec{B}$ is the magnetic field at the location of the particle. Strong magnetic fields and large gradients of magnetic fields provided by the array of magnets 102 and 103 can apply a large force of $\vec{F}_B$ to the magnetic particle than the case of sandwiching magnets without alternating dipoles or a magnet with a checkerboard pattern of magnetic dipoles positioned on only one side of the channel 506.

Accordingly, referring back to FIG. 4, the arrangement of magnetic dipole moments 231, 232, 252, and 252 can provide a strong magnetic force for isolating particles. For example, when sample fluid flows in direction 412 of channel 506, magnetic particles or particles 420 with attached magnetic beads 422 can experience a strong magnetic force $\vec{F}_B$ and become attracted towards either the array of magnets 102 or 104. On the other hand, particle 430, is not magnetic and does not experience the magnetic force $\vec{F}_B$, and therefore flows through channel 560 without becoming attached to walls 440 of the microfluidic channel layer 204. For example, the particles 420 can be abundant blood cells and the particles 430 can be target tumor cells. In the above approach, the blood cells can be effectively depleted while the target tumor cells pass through the channel 506.

The strong magnetic fields and large gradients of the magnetic fields of the magnets 231, 232, 251 and 252 can lead to a higher probability of particles 420 becoming attached to walls 440. Moreover, the relatively stronger magnetic fields can allow the fields to extend a relatively longer distance. Thus, the magnets 231, 232, 251 and 252 can efficiently attract particles 420 with attached magnetic beads 422 at a relatively longer distance. The long distance allows the presence of walls 440 (e.g., floor and ceiling of channel 506), plate 202 (e.g., glass plate) and plate 450 (e.g., glass plate) between the magnets 231, 232, 251 and 252 and the channel 506, respectively, and thereby avoiding direct contact of the sample fluid with the magnets 231, 232, 251 and 252. Accordingly, particles 420 do not get directly attached to the magnets 231, 232, 251 and 252, and the particles 420 can later be easily removed from the walls 440 by removing the magnets 231, 232, 251 and 252. In this approach, the particles 420 can be easily isolated and collected, while the magnets can be easily reused for other sample fluids without a cleansing process. In addition, the presence of walls 440, plate 202 and plate 450 can reinforce the structural rigidity of the microfluidic device 110.

In come embodiments, the channel 506 can have a height 451 of 50 μm, or 0.1 mm or more (e.g., 0.2 mm or more, 0.5 mm or more, 1 mm or more 1.5 mm or more) due to the long range of magnetic fields provided by the magnets 231, 232, 251 and 252. A larger height 451 can lead to a higher throughput of the sample fluid. Therefore, by increasing the height 451, which is possible due to the strong magnetic force, the system 100 can provide a high throughput isolation of particles. The height 451 can also be selected depending on the diameter (e.g., 40 μm) of the largest particle in the sample fluid. For example, the height 451 can be at least 20% larger than the largest diameter. In some cases, the channel 506 can have a height between 50 μm and 5 mm (e.g., between 50 μm and 1 mm, between 1 mm and 2 mm, between 2 mm and 3 mm, between 3 mm and 4 mm, or between 4 mm and 5 mm). Correspondingly, the distance between the arrays of magnets 102 and 104 can be between 50 μm and 5 mm.

The long range of magnetic fields can attract particles 420 even with the presence of the thicknesses of plates 202 and 450 and walls 440. In certain embodiments, the thicknesses of plates 202 and 450 can be 300 μm or more (e.g., 500 μm or more, 750 μm or more, 1 mm or more, 1.5 mm or more). The thickness of walls 440 can be 100 μm or more (e.g., 300 μm or more, 500 μm or more, 750 μm or more, 1.0 mm or more).

Figures 5A, 5B:
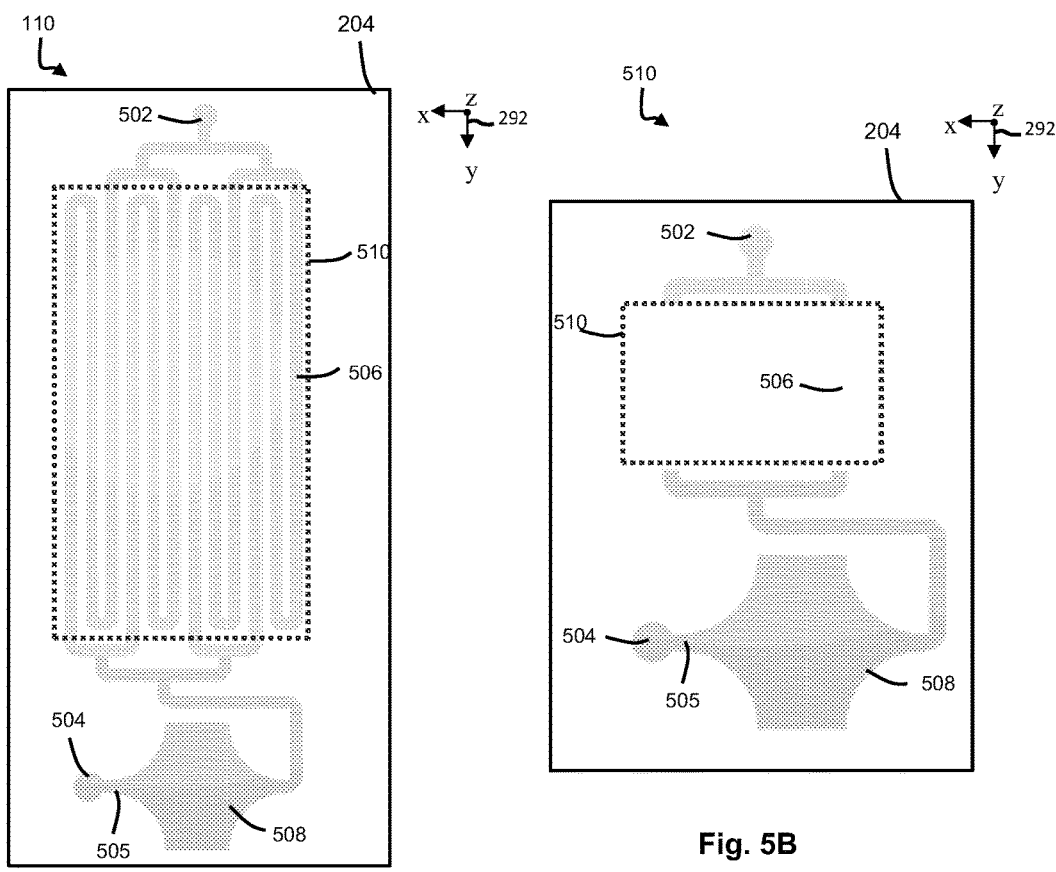
FIG. 5A is a schematic diagram showing an example of a microfluidic device.
FIG. 5B is a schematic diagram showing another example of a microfluidic device.

FIG. 5A is a schematic diagram showing the microfluidic device 110 according to coordinate 292. The microfluidic device 110 can be configured to receive sample fluid through its inlet 502. The sample fluid can flow from the inlet 502 towards outlet 504. During the flow, the sample fluid passes one or more channels 506 and then through a particle capture zone 508. The arrays of magnets 102 and 104 sandwich a region 510 of the one or more channels 506. Thus, the magnetic fields provided by the arrays of magnets 102 and 104 can isolate magnetic particles or particles with attached magnetic beads as the sample fluid passes through the one or more channels 506. Remaining particles that are not attracted by the magnets or particles with attached beads that do not get attached to walls by chance flow into the particle capture zone 508. In this example, a channel 506 has one or more windings to extend the length of the channel 506 to capture as many particles with attached beads as possible. This can lead to a high enrichment of particles 430.

Particles that pass through the particle capture zone 508 reach outlet 504 by way of a fluid manifold 505, which is positioned between the particle capture zone 508 and the outlet 504. In this example, the fluid manifold 505 is a passage between the particle capture zone 508 and the outlet 504.

FIG. 5B is a schematic diagram showing another example of a microfluidic device 510. In this example, a channel 506 is a straight channel without any winding. Such a configuration can be easier to fabricate than the design shown in FIG. 5A. Although, the channel 506 of the microfluidic device 510 has a relatively shorter length than the case shown in FIG. 5A, the isolation of particles with attached magnetic beads can be sufficiently effective due to the strong magnetic force provided by arrays of magnets 102 and 104 sandwiching region 510. Accordingly, the design and arrangement of the arrays of magnets 102 and 104 can lead to a simpler design of a microfluidic device with easier and reduced costs of manufacturing.

In some embodiments, herringbone mixers (also referred as "chaotic mixers") can be structured on the floor or ceiling within channel 506 to generate turbulence in the flow of the sample fluid. The turbulence can increase the chance of particles being located closer to the top or bottom walls of the channel(s), and thereby becoming attracted to the magnets. However, when the arrays of magnets 102 and 104 as described herein are positioned above and below the microfluidic device, the number of herringbone mixers can be reduced or eliminated due to the presence of strong magnetic forces provided by the magnets. This approach can be advantageous by simplifying the fabrication process and/or cost due the reduction or absence of the herringbone mixers.

Figure 6A:
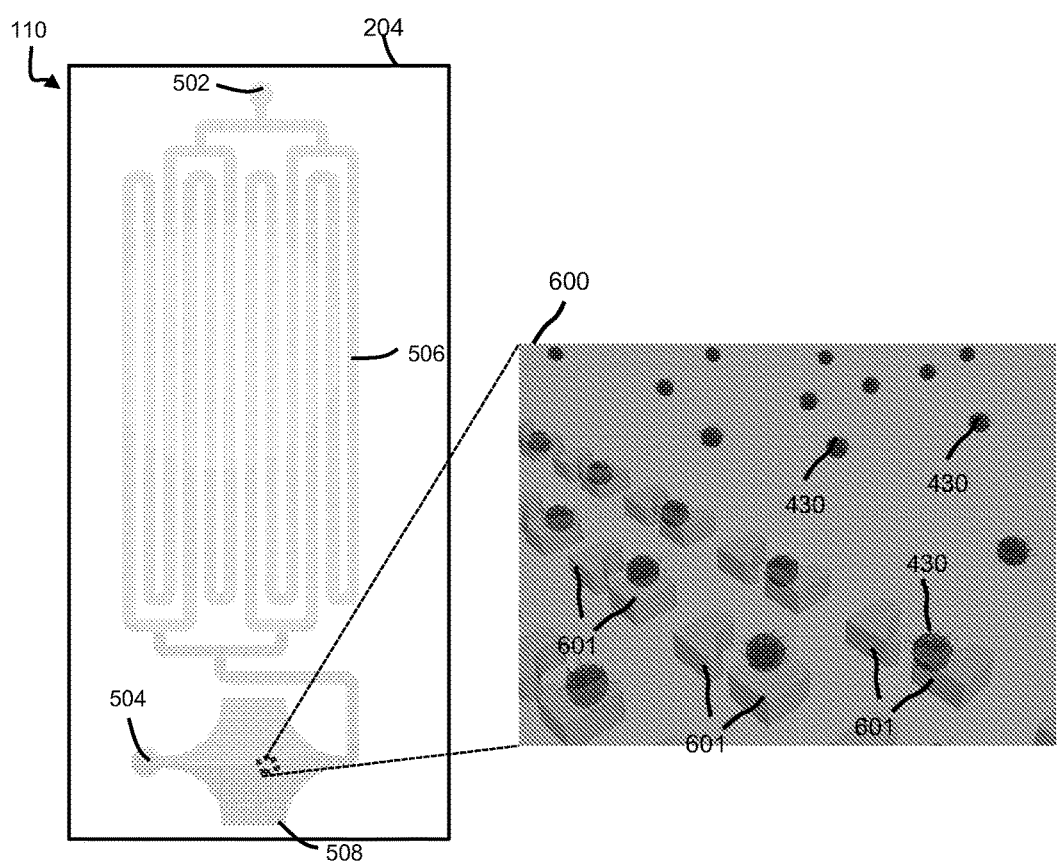
FIG. 6A is a schematic diagram showing a portion of the microfluidic device described in FIG. 5A.

FIG. 6A is a schematic diagram showing a portion of the microfluidic device 110 described in FIG. 5A. Image 600 is a zoomed in view of the particle capture zone 508, which includes a plurality of particle capture sites 601. As the sample fluid flows towards the outlet 504, remaining particles 430 can be captured in the plurality of particle capture sites 601. In some embodiments, each particle capture site 601 can include a receptacle sized to receive and confine one or more of the remaining particles 430. For example, in some embodiments, a single particle capture site 601 can have a receptacle having a size similar to a size of a target among the remaining particle 430. For instance, the receptacle can have a width, height, or cross-section approximately equal to a width, height, or cross-section, respectively, of one of the remaining particles. As an example, the receptacle can have a width that is between about 10 μm to 50 μm. In some cases, the size of the receptacle can be larger than an average diameter of the remaining particles 430 (e.g., having a size 10% larger, 20% larger, 30% larger, 40% larger, 50% larger, or more than 50% larger than the size of the target among the remaining particles 430). In some cases, the cross-section of the receptacle can be larger than an average cross-section of the remaining particles 430 (e.g., a cross sectional area 10% larger, 20% larger, 30% larger, 40% larger, 50% larger, or more than 50% larger than the cross-sectional area of the target among the remaining particles 430). In some cases, the shape of the receptacle can be similar to the shape of the expected shape of the remaining particles 430. In example, in some cases, the shape of the receptacle can be generally circular, ovular, or elliptical, depending on the shape of the remaining particles 430. In some implementations, the receptacles of one or more of the particle capture sites can each be sized to receive and contain a single one of the remaining particles 430. This arrangement allows individual remaining particles 430 to travel into a particle capture site 601, and become trapped within the particle capture site 601. The trapping can be due to the physical size and shape of the particle capture site 601.

Figure 6B:
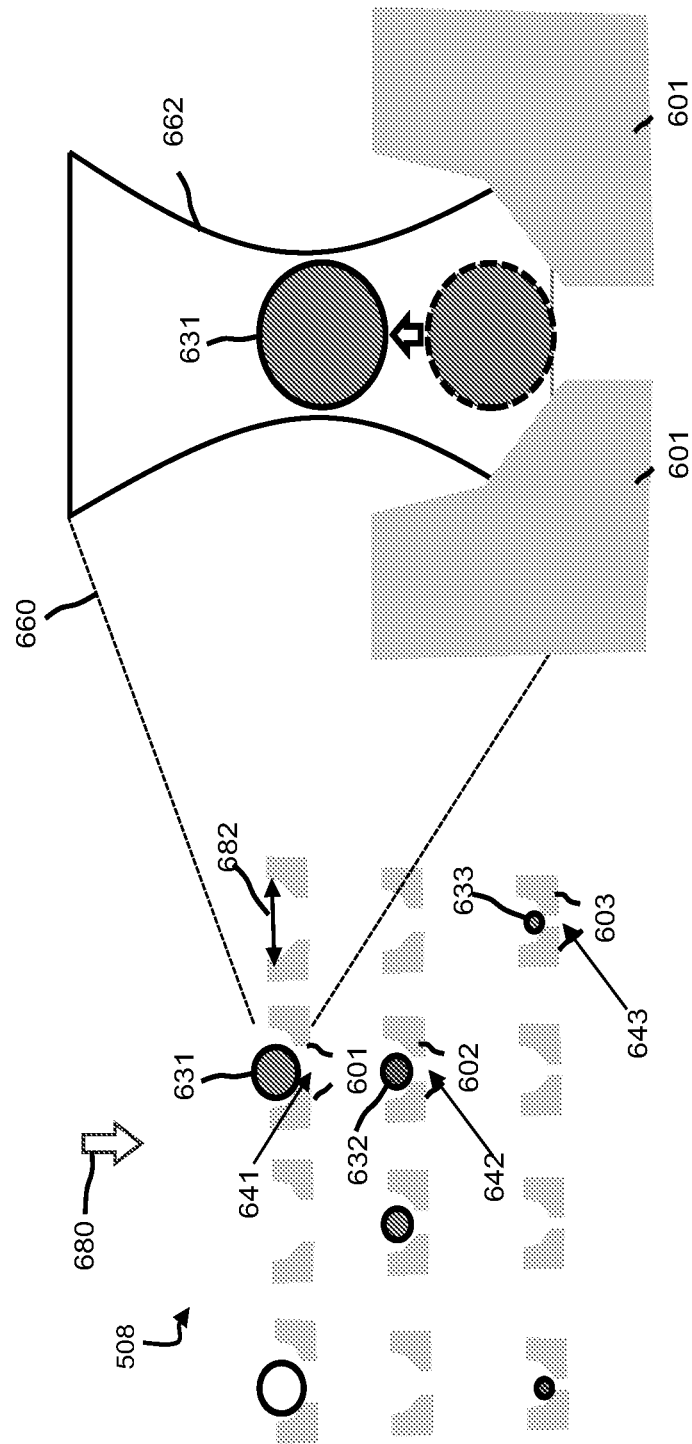
FIG. 6B is a schematic diagram showing a top view of an example of a particle capture zone.

FIG. 6B shows a top view the particle capture zone 508. In this example, the sample fluid flows in direction 680. In some embodiments, the particle capture zone 508 includes a plurality of particle capture sites 601, 602, and 603 of different sizes. For example, the particle capture site 601 has two walls with an opening 641 in between. The separation 682 between the two walls of site 601 defines a receptacle, which can be can be about 5% to 15% larger (e.g., 10% to 20% larger, 15% to 25% larger, 20% to 30% larger, 30% to 40% larger) than the diameter of target particle 631. The separation 682 can allow the particle capture site 601 to capture a single particle 631.

On the other hand, a width of opening 641 can be about 10% to 20% smaller (e.g., 20% to 30% smaller, 30% to 40% smaller) than the diameter of target particle 631. The opening 641 can allow particles smaller than the particle 631 to pass through the particle capture site 601 without being captured. For example, particles 632 and 633, being smaller than particle 631, passes particle capture sites 601. The particle 632 can be captured by particle capture site 602, which has an opening 642 for allowing the passage of particles smaller than particle 632. The particle 633 can be captured by particle capture site 603, which has an opening 643 for allowing passage of particles smaller than the particle 633. The openings 641-643 can also mitigate clogging of particle capture sites 601-603. Generally, the size of each particle capture site can be selected so that the site can dominantly capture a single particle. In this approach, the particle capture sites 601-602 can function as a size-based sorter. In some cases, the separation 682 and the opening 641 can be aligned parallel or substantially parallel to a direction of fluid flow in the particle capture zone 508 (e.g., within 5°, within 3°, within 1°), such that the receptacle and the opening 641 of each particle capture site are also aligned parallel or substantially parallel to a direction of fluid flow in the particle capture zone 508.

In some embodiments, a plurality of particle capture sites with identical dimensions can be arranged in one or more rows. For example, the particle capture sites 601 can be arranged in multiple rows of 30 or more (e.g., 10, 25, 50, 75, 100, 250, 500 or more, e.g., 1000 or more). Each row can include particle capture sites 601 of 25, 50, 75, 100, 150, 250 or more (e.g., 500 or more, 1000 or more).

Generally, a particle capture site can capture a particle due to the physical shape of the particle capture site rather than relying on binding moieties. This approach can be advantageous, because the captured particle can be easily manipulated as will be described in further detail below. On the other hand, a particle captured utilizing binding moieties, e.g., antibodies, can be difficult to detach from a capture site for subsequent manipulation and characterization. Accordingly, in some embodiments, instead of binding moieties, particle capture sites can be coated with surfactants such as Pluronic® F-127, Tween® 80, Tween® 20, bovine serum albumin (BSA), and other cell culture level surfactant to reduce sticking of particles onto the particle capture sites. In certain embodiments, the particle capture sites can be made from glass, plastic, acrylic glass, poly-methyl methacrylate (PMMA), or other materials that reduce non-specific binding of particles to the surfaces of the particle capture sites as well as the walls (including floor and ceiling walls) of the entire microfluidic device.

Figure 6C:
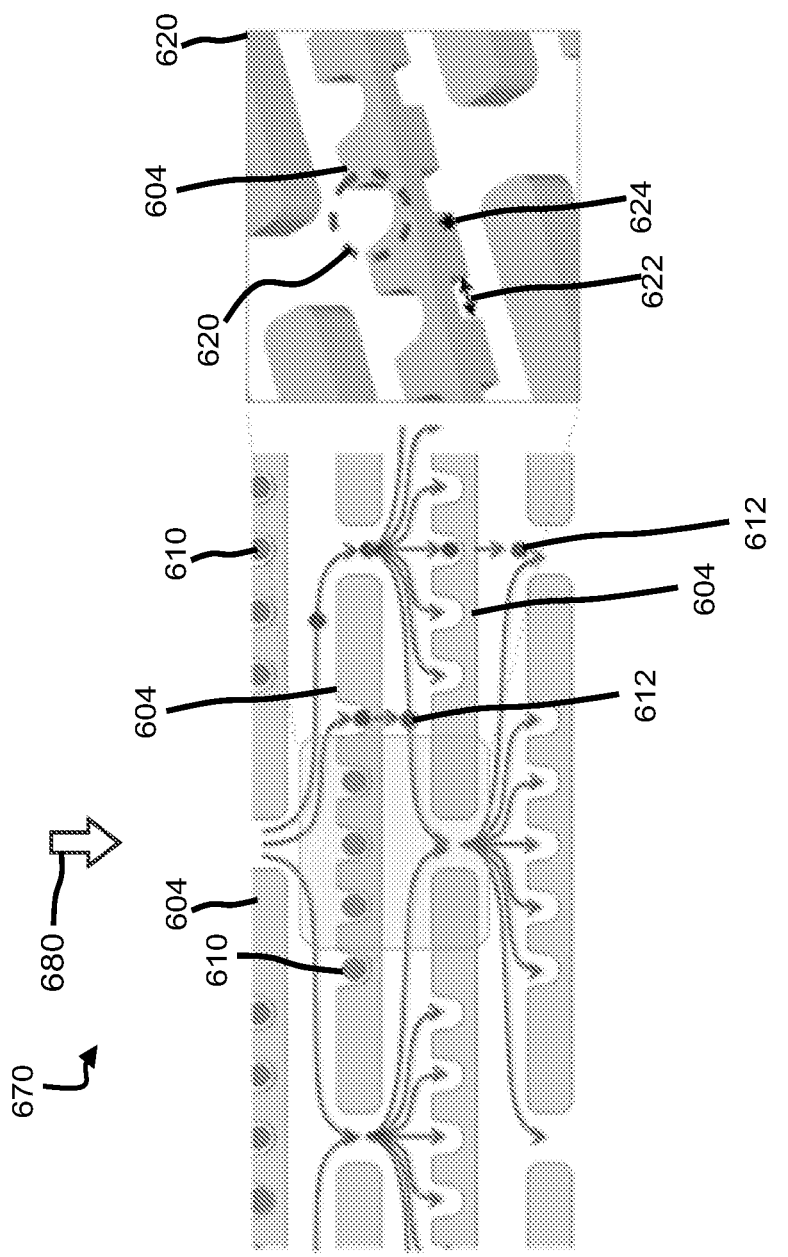
FIG. 6C is a schematic diagram showing another example of a particle capture zone.

FIG. 6C is a schematic diagram of another example of a particle capture zone 670, which includes a plurality of particle capture sites 604. As sample fluid flows in direction 680, particle capture sites 604 can capture particle 610 while allowing smaller particle 612 to pass through. View 620 shows a zoomed image of a portion of the particle capture zone 670. As illustrated, each particle capture site 604 is defined by a recess or notch 620 which has a size configured to capture a single particle 610. The particle capture site 604 also has an opening with width 622 and height 624 that allows particle 612 to pass through. The size of notch 620, width 622 and height 624 can be selected based on the diameters of particles 610 and 612 to be captured and passed through.

As mentioned earlier, system 100 can include the tweezer device 120, which can be used for manipulation of particles in the sample fluid. Referring back to FIG. 6B, side-view 660 depicts a zoomed side-view (instead of a top view) of particle capture size 601 with its captured particle 631. In this example, tweezer device 120 is an optical tweezer utilizing a focused optical beam 662 to trap the particle 631 within the beam waist of the optical beam. The optical beam 662 is focused by a microscope objective (not shown). Electric field gradients of the optical beam attract the particle 631 within the beam waist. The particle 631 can be lifted up and moved around by moving the position of the focused beam waist in 3-dimensional space. The focused beam can be moved by displacing the microscopic objective or adjusting the beam direction using actuators. The displacement or adjustment can be carried out manually by a user or through a computer controlled motor as described below.

Optical tweezers for manipulating materials that are useful in the present methods and systems are described, for example, in U.S. Pat. Nos. 7,104,659, and 7,759,635. Acoustic tweezers for manipulating materials that are useful in the present methods and systems are described, for example, in Ding, Xiaoyun, et al., "On-chip manipulation of single microparticles, cells, and organisms using surface acoustic waves." Proceedings of the National Academy of Sciences 109.28 (2012): 11105-11109, and in Li, Ying, et al. "A simple method for evaluating the trapping performance of acoustic tweezers." Applied physics letters 102.8 (2013): 084102. The contents of each of the foregoing patents and publications are incorporated herein by reference in their entirety.

Figure 7A:
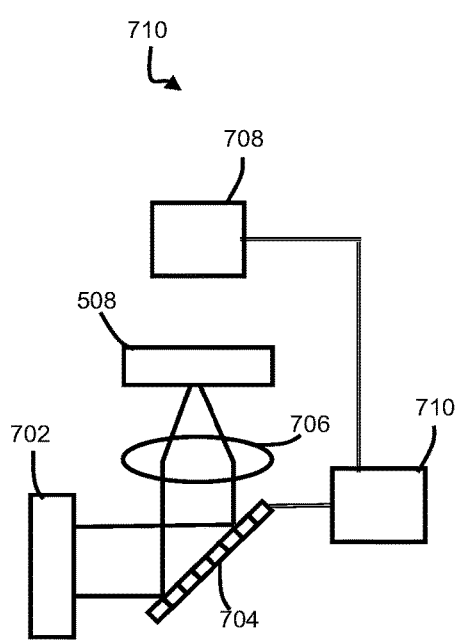
FIG. 7A is a schematic diagram showing an example of a tweezer device.

FIG. 7A is a schematic diagram of an example of a tweezer device 710 that can be used in system 100. The tweezer device 710 can include an optical source (e.g., laser source) to provide an optical beam. A mirror 704 can reflect the optical beam towards a lens device 706, which focuses the optical beam into one or more particle capture sites (not shown) in particle capture zone 508. Other optical components that can be used for beam shaping and steering are not shown, but are well known to those of skill in this field. In some embodiments, the lens device 706 can be a single microscopic objective used to focus the optical beam for optical trapping. In certain embodiments, the lens device 706 can be a microlens array which splits the optical beam into a plurality of focused beams. Each of the focused beams can be used for optical trapping of particles captured in the particle capture zone 508. In this approach, the tweezer device 710 can provide a plurality of optical traps.

The mirror 704 can be a planar mirror for directing the optical beam towards the lens device 706. In some embodiments, the mirror 704 can be a spatial light modulator (SLM), which can direct different portions of the optical beam independently. For example, the mirror 704 can be an array of MEMS mirrors, where each mirror can steer different portions of the optical beam through the lens device 706 in order to manipulate different optical traps independent of one another.

The tweezer device 701 is often used in conjunction with an imaging device 708 that can be used to image the particle capture zone 508. For example, the imaging device 708 can include a 2D charge-coupled device (CCD) camera that can monitor individual particle captures sites and captured particles in the particle capture zone 508. In some embodiments, the imaging device 708 can send image data to a controller 710.

In certain embodiments, the controller 710 can process and visualize the image data on a screen. A user may then monitor the screen and input information using an input device (e.g., keyboards, mouse, and touchscreen) so that the controller 710 sends out control signals to the mirror 704 and/or other optical components in the tweezer device 710. For example, the user can visually monitor a touchscreen and select a target particle through the touch screen for analysis. In certain embodiments, the control signals can activate actuators, for example, for controlling MEMS mirrors in mirror 704 or other optical components to steer a focused optical beam to trap the selected target particle for manipulation.

In some embodiments, the controller 710 can process the image data and select a target particle to trap and manipulate without an input from the user. For example, the controller 710 can determine which target particles to select based on the size of the corresponding particle site and/or based on a reporter group or marker, e.g., color, fluorescence, or radioactivity, on or of the particles. For example, a color can be due to staining of a specific type of particles. The controller 710 can compare the size and color information to library information stored in the controller 710 to determine the selection and manipulation as is known in the relevant field.

Figure 7B:
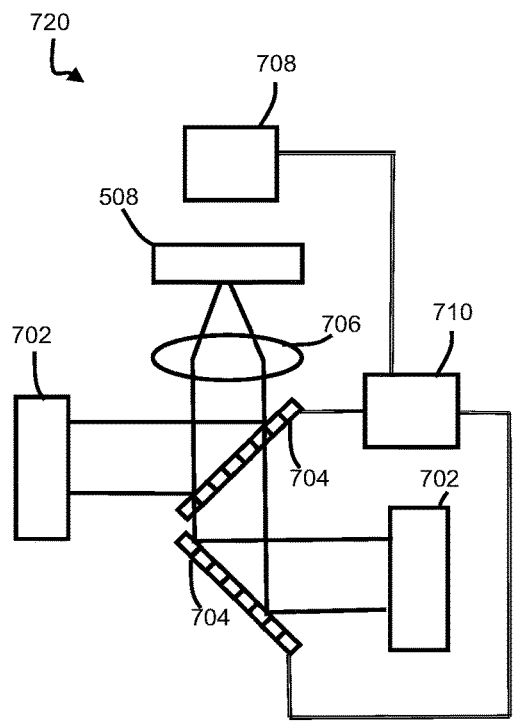
FIG. 7B is a schematic diagram showing another example of a tweezer device.

FIG. 7B is a schematic diagram of another example of a tweezer device 720, which can be used in system 100. The tweezer device 720 includes two optical sources 702 which two beams can be used to interfere and form an optical lattice. A focused beam point in the optical lattice can be used to capture and manipulate a particle in particle capture zone 508. In some embodiments, mirrors 704 can include SLMs that can manipulate individual lattice points in the optical lattice for controlling individual or a group of trapped particles. In certain embodiments, the tweezer device 720 can use computer-generated holograms to create a pattern of the optical lattices to capture selected particles.

Figure 8:
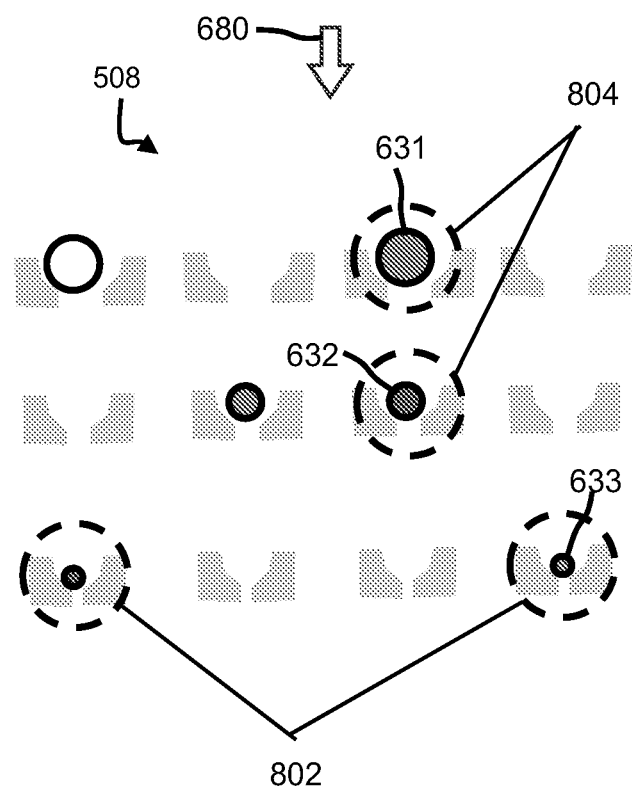
FIG. 8 is a schematic diagram showing a top view of the particle capture zone described in relation to FIG. 6B.

Referring to FIG. 8, a schematic diagram shows the top view of the particle capture zone 508 described in relation to FIG. 6B. In some embodiments, tweezer device 120 can be configured to trap a single particle (e.g., particle 631) at a given time, lift up and release the particle for subsequent analysis. In certain embodiments, the tweezer device 120 can be configured to trap a plurality of particles at the same time. For example, particles in regions 804, which have different sizes, can be trapped, lifted up and displaced at the same time. As another example, particles in regions 802, which have the same size, can be trapped, lifted up and displaced at the same time. In some example, the tweezer device 120 can select particles with same stain color for subsequent analysis.

Figure 9:
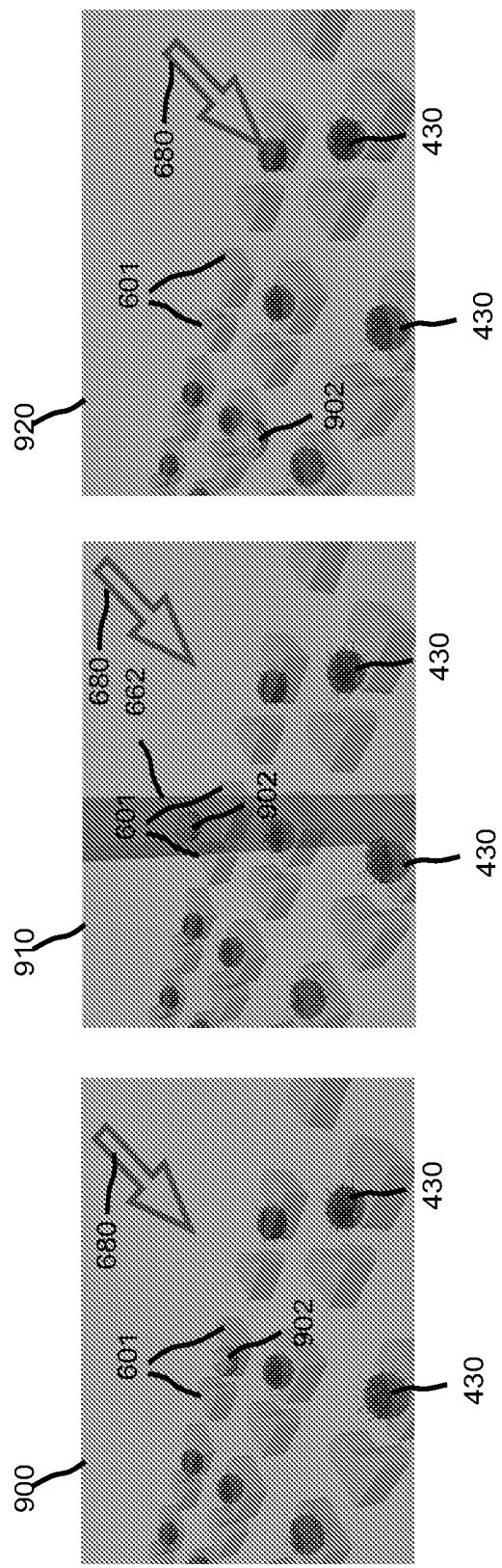
FIGS. 9A-9C are schematic diagrams of images showing a process for manipulating a target particle.

FIGS. 9A-9C are schematic diagrams of images showing a process for manipulating a target particle. In FIG. 9A, target particle 902 in particle capture site 601 is stained in a green color. The staining can be achieved before the sample fluid is introduced into microfluidic device 110. In some embodiments, the staining can be achieved after the sample fluid is in microfluidic device 110 and the target particle 902 is captured in particle capture site 601. For example, the staining process can include attaching targeting particles 902 (e.g., intracellular, extracellular markers) with fluorescent antibodies, drugs, or chromophores. In FIG. 9B, optical beam 662 is focused to optically trap the target particle 902. By moving the beam waist of the optical beam 662 upwards, the trapped target particle 902 can be lifted, while other particles 430 remain captured.

In FIG. 9C, the optical beam 662 is removed so that target particle 902 is released from trapping. When flushing fluid flows in direction 680, the released target particle 902 can follow the follow and become transported to outlet 504. At this step the flush fluid can be the same or different from the sample fluid depending on the analysis method. For example, in some applications, it can be desirable to use a flush fluid without any particles to improve purity of the collected samples. In certain embodiments, the flush fluid can be same sample fluid without changing to another fluid. The absence of changing fluid can allow fast collection of samples. In some embodiments, the flush fluid can be used for high throughput application. In certain embodiments, the optical beam 662 can move the target particle 902 with high precision to a specific site for analysis.

Figure 10:
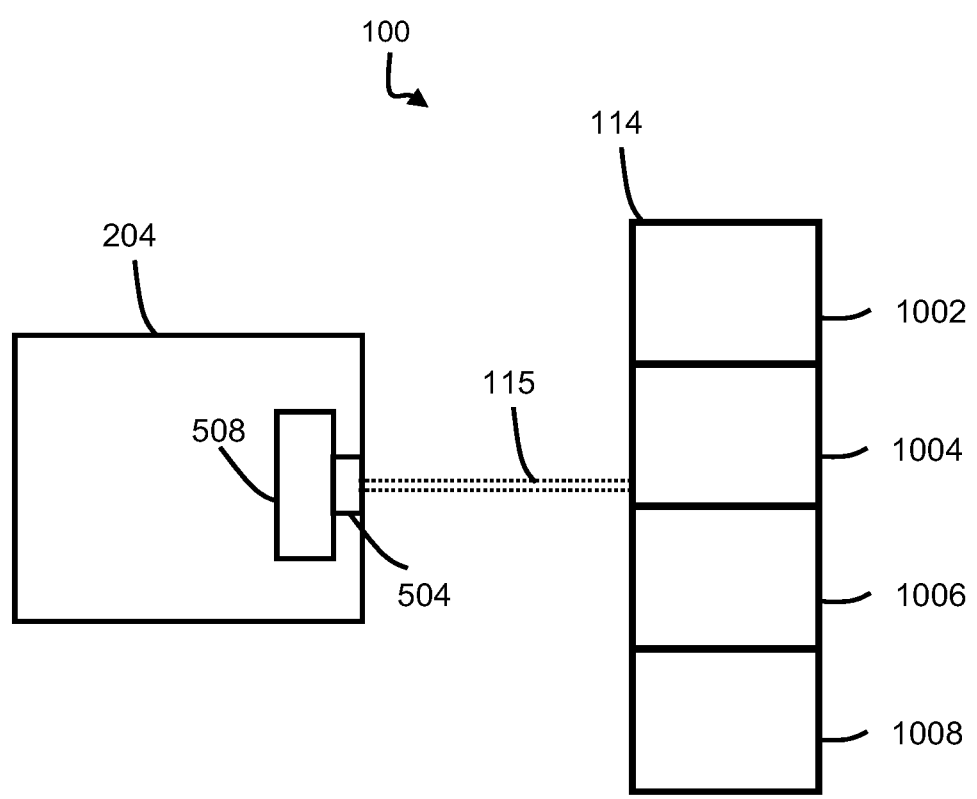
FIG. 10 is a schematic diagram showing a portion of the system described in FIG. 1.

FIG. 10 is a schematic diagram showing a portion of system 100. Particles can reach outlet 504 by flowing within sample fluid. In some embodiments, particles selected and released by tweezer device 120 can reach the outlet 504 by the flushing or washing fluid. These particles can be transported to receiver device 114 through coupling 115. In certain embodiments, the receiver device 114 can include a plurality of containers 1002-1008. Each container can be used to receive and contain a single particle, a group of particles, same type of particles or different type of particles for characterization. For example, tweezer device 120 can trap and release a single target particle which is transported to the receiver device 114. After the container receives the transported single target particle, a user or a motorized staged can adjust the containers so that container 1004 can receive the next samples. For example, next the tweezer device 120 can trap and release target particles which are transported to the receiver device 114. After receiving a plurality of target particles, the container 1004 can be removed for characterization of the contained target particles.

Fabrication

Microfluidic device 110, and other similar devices as described herein, can be manufactured using a variety of fabrication processes, e.g., processes known to those of skill in the relevant fields. For example, in some embodiments, an injection molding process is used to fabricate the microfluidic device 110. For example, material such as glass, PDMS, or melted plastic can be injected into a predetermined mold defining inlet 502, outlet 504, channels 506, particle capture zone 508, and its particle capture sites. After cooling and hardening of the injected material, further process such as drilling and/or cutting can be implemented to refine the pattern formed in the microfluidic device 110. The patterned layer is then bonded to another flat substrate (e.g., glass, plastic, PDMS) to form a complete, sealed microfluidic device 110.

In some embodiments, etching or photolithography processes can be implemented to fabricate the microfluidic device 110. For example, a film of PDMS can be spin coated on a substrate, and then light is used to transfer a pattern from a photomask to the PDMS film. The pattern can define the various openings (e.g., inlet 502, outlet 504, channels 506, particle capture zone 508 and particle capture sites) of the microfluidic device 110.

In certain embodiments, imprint lithography can be implemented to fabricate the microfluidic device 110. For example, a mold defining various openings (e.g., inlet 502, outlet 504, channels 506, particle capture zone 508 and particle capture sites) can be pressed against an imprint resist while being cured by heat or ultra-violet (UV) light.

In some implementations, during operation of the system 100, the microfluidic device 110 can be mounted on a device holder. The holder can include two slabs (e.g., a top and bottom slab), with each slab containing the magnet arrays 102 and 104. The microfluidic device 110 can be positioned and held in place between the slabs through a mechanical locking mechanism (e.g., through screws, notches, pegs, pins, or clamps), the magnetic pulling between the magnet arrays, or both. To define the fluidic ports, pairs of cylindrical magnets (e.g., magnets 210 and 212; and/or magnets 220 and 222) can be aligned at the openings 502 and 504 of the microfluidic device 110. The fluidic ports can be secured to the microfluidic device through the magnetic pulling between the pair of magnets 210 and 212, and/or the pair of magnets 220 and 222.

By separating the microfluidic device and the magnetic system, this modular scheme can simplify the device fabrication and facilitate the system setup. It can also reduce the operation cost, as the device holder, magnet arrays and the magnetic ports can be repeatedly used.

General Methodology

Figure 11:
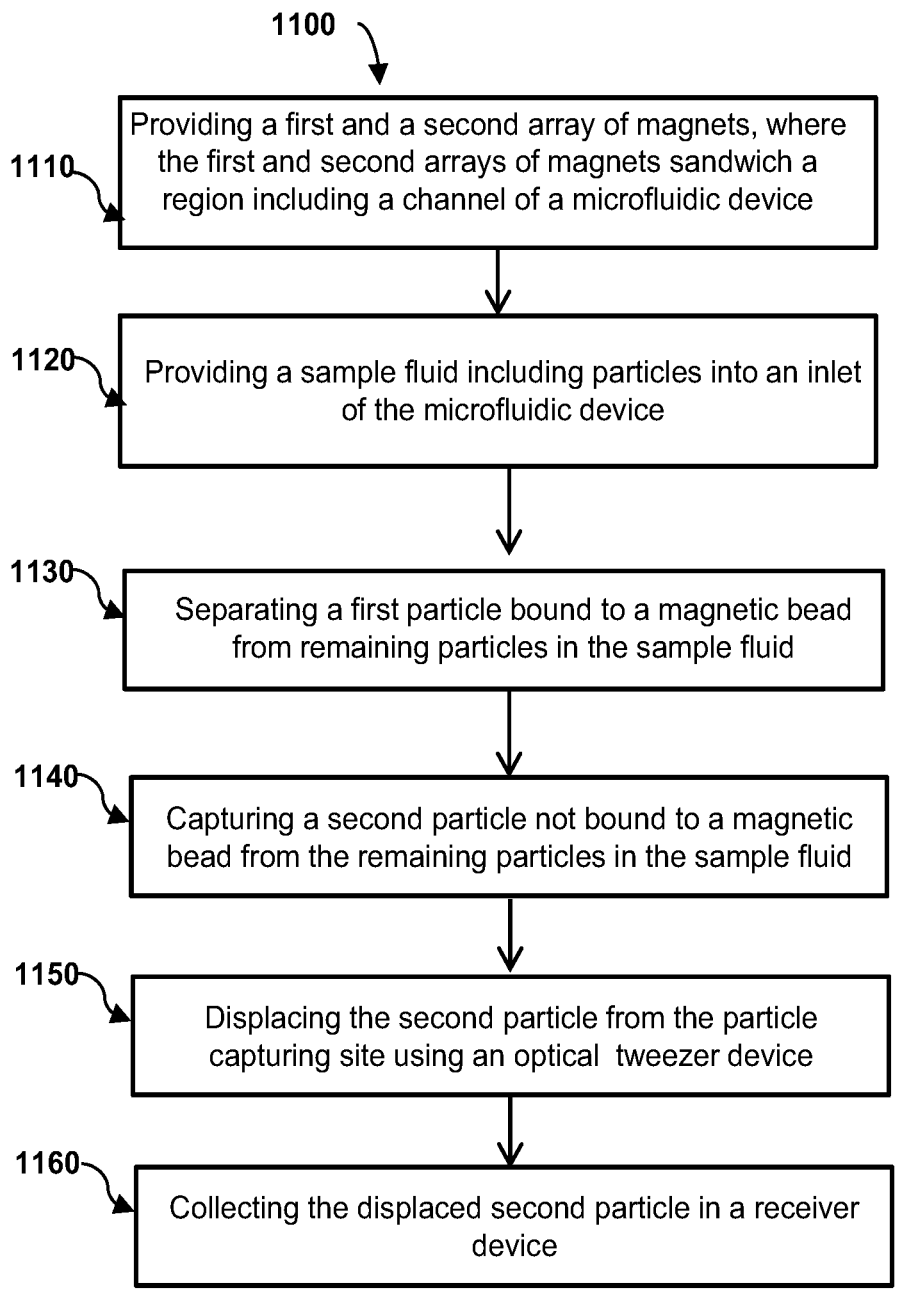
FIG. 11 is a flow chart depicting exemplary operations for isolating particles.

Referring to FIG. 11, a flow chart 1100 depicts examples of operation steps for isolating particles using a system described herein, e.g., system 100. Operations include providing a first and a second array of magnets 102 and 104, where the first and second arrays of magnets 102 and 104 are positioned to sandwich a region including a channel 506 of a microfluidic device 1110 (1110). In some embodiments, the first and second arrays of magnets 102 and 104 include magnetic dipole moments arranged in alternating order, such that adjacent magnets have dipole moments aligned in opposite directions. The magnets of the first and second array can include magnets made of materials such as NdFeB, SmCo, FePt, $MnFe_2O_4$, $CoFe_2O_4$, $NiFe_2O_4$, $ZnMnFe_2O_4$, or iron oxide.

Operations also include providing a sample fluid including particles into an inlet 502 of the microfluidic device 110 (1120). In some embodiments, the particles can include tumor cells, blood cells such as leukocytes and biomarkers. Some of these particles can be bound by magnetic beads and/or fluorescent beads. In certain embodiments, some of the particles can be stained. For example, cancer cells can be pre-stained with 1:2000 Hoescht 33258 (Invitrogen).

A first particle bound to a magnetic bead can be separated from remaining particles in the sample fluid (1130). This can be achieved by flowing the sample fluid through the channel 506, where the first particle is separated by magnetic fields provided in the region between the first and second arrays of magnets 102 and 104. Strong magnetic field strength and large gradients of magnetic fields can provide a long range force to attract particles bounded with magnetic beads.

Operations also include capturing a second particle not bound to a magnetic bead from the remaining particles in the sample fluid into a particle capture site of the microfluidic device 110 (1140). In some embodiments, the microfluidic device can include a plurality of particle capture sites of 100 or more (e.g., 500 or more, 1000 or more, 10000 or more). At least some of the particle capture sites can have a size and shape designed to capture a single particle. Different particle capture sites can have different sized designed to capture particles with different sizes.

The captured second particle can be displaced using an optical tweezer device (1150). The optical tweezer device can be configured to trap a single particle. In certain embodiments, the optical tweezer device can provide multiple optical traps configured to trap multiple particles at the same time. The optical tweezer device can displace the second particle out of its particle capture site. Then the displaced second particle can be transported to an outlet 504 by releasing it from the optical tweezer device.

Operations also include collecting the displaced second particle in a receiver device 114 (1160). The released second particle in operation (1130) can be transported from the outlet 504 to a receiver device 114. In some embodiments, the receiver device 114 can include a plurality of containers, each receiving different particles released by the tweezer device 120. In this approach, a user can collect target particles in separate containers for subsequent characterization.

Hardware and Software Implementation

Figure 12:
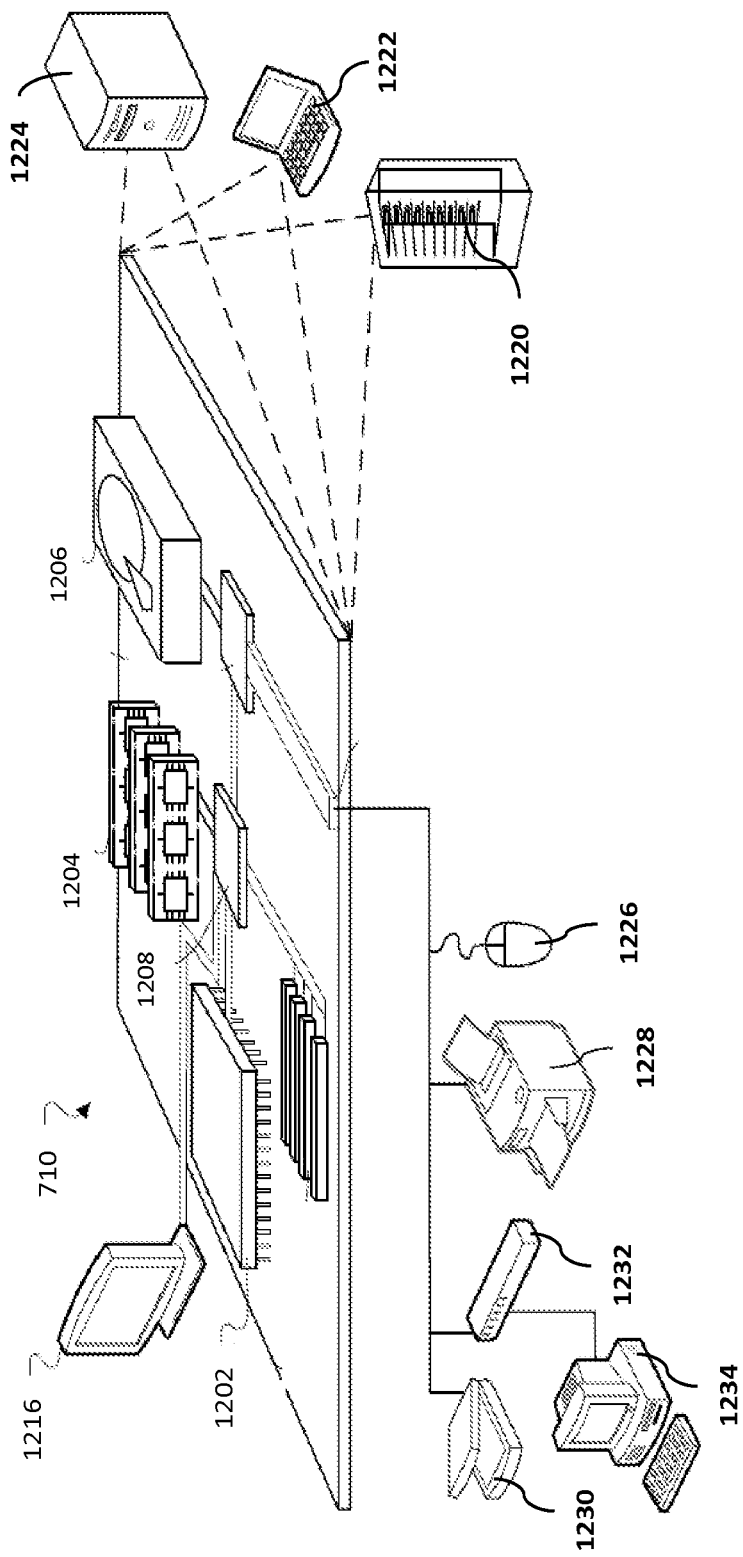
FIG. 12 is a schematic diagram showing an example of a controller.

FIG. 12 is a schematic diagram showing an example of a controller 710, which may be used with the techniques and systems described herein. As mentioned above, the controller 710 can be used to receive image data and control beam directions of a tweezer device. The controller 710 can include a processor 1202, memory 1204, a storage device 1206, and interfaces 1208 for interconnection. The processor 1202 can process instructions for execution within the controller 710, including instructions stored in the memory 1204 or on the storage device 1206. For example, the instructions can instruct the processor 1202 to identify characteristics of captured particles based on, e.g., size and color. The processor 1202 can be configured to send out control signals to adjust beam directions of the tweezer device.

The memory 1204 can store information of parameters of the tweezer device. For example, the information can relate actuator positions to focus positions of an optical beam. The storage device 1206 can be a computer-readable medium (e.g., a hard disk, an optical disk, a flash memory or solid state memory device), which can store information of characteristics (e.g., color, size, shape) of predetermined particles. The process 1202 can compare the stored information to image data to identify the types of captured particles. The storage device 2605 can store instructions that can be executed by processor 1202 described above. In certain embodiments, the storage device 2605 can store information described in relation to memory 1204.

In some embodiments, controller 710 can include a graphics processing unit to display graphical information (e.g., using a graphical user interface (GUI) or text interface) on an external input/output device, such as display 1216. The graphical information can be displayed by a display device (e.g., a CRT (cathode ray tube) or LCD (liquid crystal display) monitor) for displaying information. A user can use input devices (e.g., keyboard, pointing device, touch screen, speech recognition device) to provide input to the controller 710. For example, the input can identify which captured particle to manipulate. Based on the input, the controller 710 can control the system as described above.

Various embodiments of the systems and techniques described herein can be implemented as one or more computer programs that are executable and/or interpretable on the controller 710. These computer programs (also known as programs, software, software applications or code) include machine instructions for a programmable processor, and can be implemented in a high-level procedural and/or object-oriented programming language, and/or in assembly/machine language. For example, computer programs can contain the instructions that can be stored in memory 1204 and storage 1206 and executed by processor 1202 as described above. As used herein, the terms "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

In some implementations, the controller 710 can be interconnected with other components. For example, the controller 710 can be communicatively coupled to one or more server computers 1220, one or more laptop computers 1222, and/or one or more desktop computers 1224. As another example, the controller 710 can be communicatively coupled to one or more peripherals (e.g., input devices 1226, printers 1228, or scanners 1230). In some cases, the controller 710 can be communicatively coupled to one or more computer systems 1234 through a network (e.g., through a network switch 1232). The controller 710 can transmit data to, and received from, each of these interconnected components in order to perform some or all of the functions described above.

Generally, controller 710 can be implemented in a computing system to implement the operations described above. For example, the computing system can include a back end component (e.g., as a data server), or a middleware component (e.g., an application server), and/or a front end component (e.g., a client computer having a graphical user-interface), or any combination therefor, to allow a user to utilized the operations of the controller 710.

General Applications

Generally, system 100 can be used as a platform for isolating particles, such as rare target cells (e.g., circulating tumor cells, circulating stem cells, or fetal cells circulating in maternal blood) directly from the whole blood samples. The strong magnetic forces provided by the arrays of magnets sandwiching a microfluidic channel as described herein can be used to immuno-magnetically deplete abundant host cells such as leukocytes while enabling target cells such as cancer cells to pass through the magnetic fields. These target cells can be individually captured by physical barriers, and subsequently analyzed in situ for comprehensive and multifaceted evaluation, including single cell enumeration and imaging, molecular and genetic profiling, and drug-treatment responses. Moreover, a tweezer device can be used to lift and retrieve captured particles (e.g., cancer cells) which can be further transported for downstream off-chip analyses.

As an example, a biological sample (e.g., a blood sample, a cerebral spinal fluid sample, or any other biological sample) can include several different types of cells and other particles, only some of which may be of interest for a particular study. The system 100 can be used to immuno-magnetically deplete this biological sample, such that that unwanted cells are separated from the biological sample, while cells of interest remain in the biological sample and become immobilized within the capture zone of the system 100. Once captured, these cells can be individually cultured and/or examined in order to further investigate the properties of each cell.

In some cases, cells that have been immobilized within the capture zone can be examined through immunostaining. As an example, captured cells can be exposed to fluorescently labeled particles (also called fluorescent markers) that exhibit binding specificity to particular biomarkers of interest. These particles can include, for example, molecules having targeting moieties specific to certain biomarkers (e.g., antibodies, enzymes, cellular receptors, or other targeting molecules), in which the molecules are bound to fluorophores (e.g., phycoerythrin (PE) or fluorescein isothiocyanate (FITC)). Captured cells can be exposed to these fluorescently labeled particles, for instance, by flowing the fluorescently labeled particles across the capture zone of the system 100, such that the particles are allowed to bind to captured cells that express these biomarkers. The capture zone of the system 100 can then be examined to determine the presence of the biomarkers of interest (e.g., by optically exciting the fluorophores, capturing images of the resulting fluorescence, and observing the intensity of the resulting fluorescence). As individual cells can be captured in each of the capture sites of the capture zone, these cells can be examined for the presence or absence of the biomarker of interest with single cell resolution Thus, the system 100 can be used to receive a biological sample, increase the relative abundance of cells of interest within the biological sample through immuno-magnetic separation, and identify individual cells expressing a particular biomarker of interest. Individual cells (e.g., cells expressing the biomarker of interest) can then be collected for further study.

In some cases, implementations of this system can be used to investigate the relative population of certain types of cells within a biological sample. As an example, a biological sample may include several different types of cells. One or more of these cell types may be immuno-magnetically depleted, such that they are removed from the biological sample. The remaining cells types can be captured within the capture zone of the microfluidic device, then analyzed using immunostaining to ascertain if the captured cells express one or more particular biomarkers. The presence or absence of these biomarkers can be used to deduce the type of cells that have been captured within the capture zone. As the capture zone contains several different capture sites, each immobilizing a different individual cell, an immunostaining analysis of the capture sites of the capture zone can reveal information regarding the relative abundance of each type of cell within the biological sample. This can be useful, for example, for lymphoma detection, where several different sub-types of lymphoma each express a particular biomarker or combination of biomarkers. Implementations of this system can be used to differentiate between each of these different sub-types. Although lymphoma is provided as an example, this is merely illustrative. In practice, implementations of the system 100 can be used to differentiate between other types of disease cell sub-types, or any other type of cell.

In some applications, implementations of the system 100 can be used for drug screening. As an example, cells of interest that have been captured within the capture zone of the system 100 can be incubated, then exposed to one or more different drugs and/or incubated with drugs for varying incubation times. In some cases, these drugs can be introduced into the capture zone by flowing the drugs through the microfluidic device (e.g., by introducing the drug into an inlet of the microfluidic device, and allowing the drug to flow throughout the microfluidic device and out of the outlet of the microfluidic device. In some cases, one or more of these drugs can be introduced into the capture zone by additional inlets of the microfluidic device that are in direct fluid communication with the capture zone of the microfluidic device. The captured cells can be individually exampled before and/or after incubation with the drugs (e.g., using immunostaining) in order to ascertain the effect of those drugs on each captured cell. In some cases, different regions of the capture zone can be exposed to different drugs and/or different concentrations of drugs, such that a wide array of therapeutic conditions can be investigated simultaneously within a single capture zone.

For example, in some cases, certain regions of the capture zone can be exposed to a first concentration of a drug, while another region of the capture zone can be exposed to a second concentration of a drug. Accordingly, captured cells within each of the regions will be exposed to different concentrations of the drug. The captured cells can be individually examined before and/or after incubation with the drugs (e.g., using immunostaining) in order to ascertain the effect of varying concentrations of the drug on the captured cells.

As another example, in some cases, certain regions of the capture zone can be exposed to a first drug, while another region of the capture zone can be exposed to a second drug. Accordingly, captured cells within each of the regions will be exposed to different drugs. The captured cells can be individually exampled before and/or after incubation with the drugs (e.g., using immunostaining) to ascertain the effect of different drugs on the captured cells.

In some cases, the capture zone or region can be exposed to a gradient of different drugs and/or different drug combinations. In some cases, this can be achieved by flowing two or more drugs and/or drug concentrations in parallel across the capture zone (e.g., by introducing the drugs into the inlet 502 and/or into one or more additional inlets distributed across an end of the capture zone in a direction orthogonal to a direction of fluid flow through the capture zone). As the drugs flow across the capture zone, the drugs mix and create a gradient within the capture zone. The captured cells can be individually exampled before and/or after incubation with the drugs (e.g., using immunostaining) to ascertain the effect of different drugs and/or drug concentrations on the captured cells. In some cases, as the drugs flow across the capture zone, the drugs do not mix (or do not substantially mix) due to laminar flow. In these cases, the drugs do not create a continuous gradient. However, this combination of different drug (or drug concentration) still creates a gradient (e.g., a gradient with a discrete number of different drugs or drug concentrations) within the capture zone.

Figures 25A, 25B, 25C:
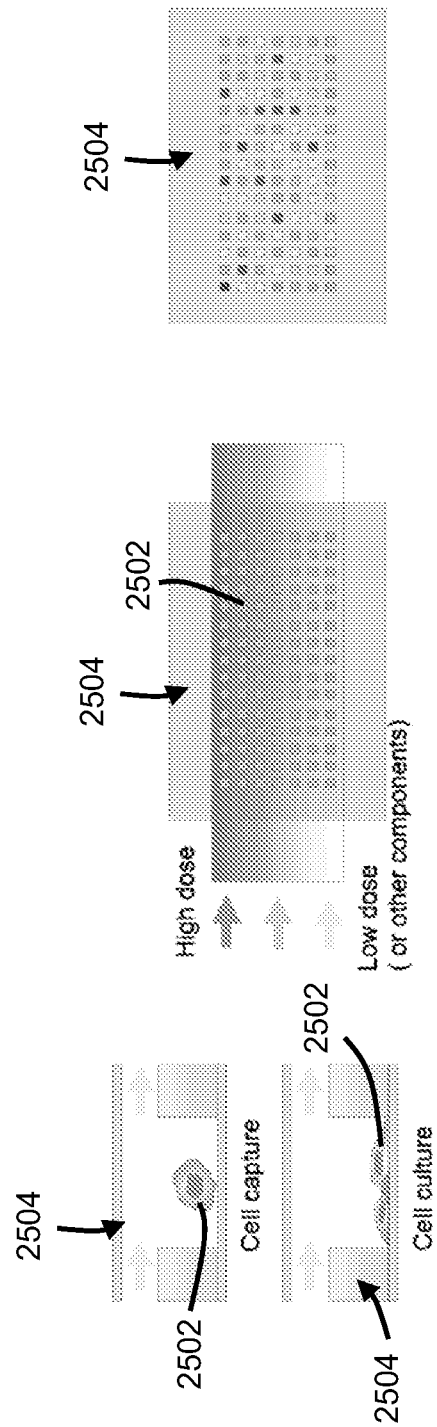
FIGS. 25A-C are diagrams showing an example drug screening process.

As an example, as shown in FIG. 25A a cell 2502 that has been captured within a capture site 2504. Once captured, the cell 2502 can be incubated within the capture site 2504. As shown in FIG. 25B, a capture zone 2506 can include an array of spatially distributed capture sites 2504. Different regimens of drugs (e.g., different concentrations of drugs) can be flowed across the capture sites 2504, such that each of the capture sites 2504 is exposed to a spatially-dependent drug regimen. As shown in FIG. 25C, the capture sites 2504 can each be analyzed (e.g., using immunostaining), in order to investigate the effect of each treatment regimen on the capture cells.

Using the system 100 for drug screen can be beneficial, for example, for assessing the effectiveness of treating various types of lymphoma Implementations of this system can be used to treat various types of lymphoma cells with one or more therapeutic drugs, then assess the effectiveness of those drugs in binding to each of the different cell types and effecting a response. Although lymphoma is provided as an example, this is merely illustrative. In practice, implementations of the system 100 can be used to assess the effectiveness of treating various other types of diseased cells.

In some applications, implementations of the system 100 can be used to screen cells through particle-cycling (e.g., antibody-cycling, enzyme-cycling, or cellular receptor-cycling). As described above, in some cases, cells that have been immobilized within the capture zone can be examined through immunostaining. For example, fluorescent labeled particles having targeting moieties specific to a first type of biomarker can be flowed across the capture zone of the system 100, such that the fluorescent particles are allowed to bind to captured cells expressing the first type of biomarker. The capture zone of the system 100 can then be examined in order to determine the presence of the first type of biomarker. After examination, the fluorescent particles bound to the captured cells can be cleaved from the captured cells (e.g., using an elution buffer or photo-cleaving), and removed from the capture zone. As a result, the captured cells remain immobilized within the capture sites, but are no longer bound to any fluorescently labeled particles. Subsequently, a second group of fluorescently labeled particles having targeting moieties specific to a different type of biomarker can be flowed across the capture zone of the system 100, such that the second group of fluorescently labeled particles are allowed to bind to captured cells expressing the second type of biomarker. The capture zone of the system 100 then can be examined in order to determine the presence of the second type of biomarker. In this manner, the same captured cells can be investigated using multiple "cycles" of fluorescently labeled particles, where each cycle reveals the presence or absence of a different biological marker. In some cases, each cycle can include multiple different types of fluorescently labeled particles, each specific to a different particular biomarker, and each fluorescing at a different particular wavelength. In this manner, the presence or absence of several different biomarkers can be examined simultaneously. After examination, these particles can be cleaved from the captured cells, and one or more additional fluorescently labeled particles can be flowed across the captured cells. This cycle can be repeated any many times as desired (e.g., one, two, three, four, or more times) to examine the presence or absence of any number of different biological markers.

Figure 26A:
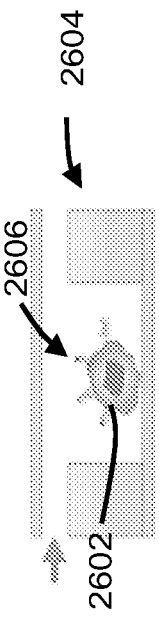
FIGS. 26A-D are diagrams showing an example particle cycling process.
Figure 26B:
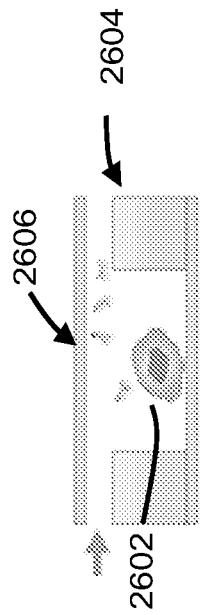
Figure 26C:
Figure 26D:
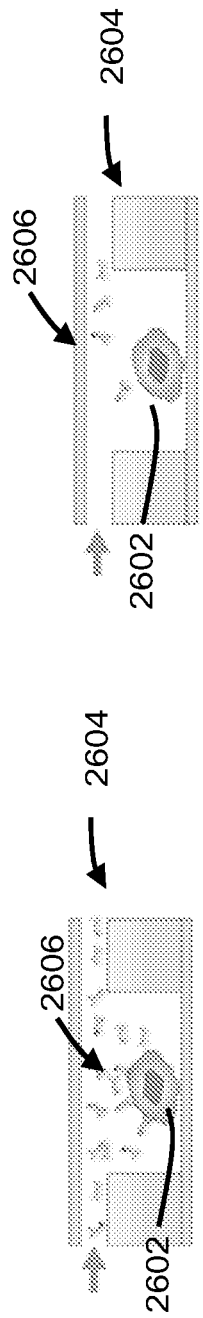

As an example, as shown in FIG. 26A a cell 2602 that has been captured within a capture site 2604. As shown in FIG. 26B, once the cell 2602 has been captured, a first fluid sample containing a first type of fluorescently labeled particle 2606 is flowed across the capture site 2604. The fluorescently labeled particles 2606 are specific to a particular biomarker expressed by the cell 2602. Thus, as shown in FIG. 26C, one or more of these fluorescently labeled particles 2606 adhere to the cell 2602. While the fluorescently labeled particles 2606 are adhered to the cell 2602, the capture sites 2604 can each be analyzed (e.g., using immunostaining), to investigate the presence or absence of the fluorescent marker, and consequently, the presence or absence of the biomarker on the cell 2602. As shown in FIG. 26D, an elutant is flowed across the capture site 2604. This elutant cleaves the fluorescently labeled particles 2606 from the cell 2602, removing the from the cell 2602 and from the capture site 2604. Subsequently, a second fluid sample containing a second type of fluorescently labeled particle is flowed across the capture site 2604, where the second type of fluorescently labeled particles are specific to a different particular biomarker expressed by the cell 2602. Thus, this staining and cleaving process can be "cycled" to examine the presence or absence of any number of different biological markers.

Although the examples of applications described herein use fluorescently labeled particles, some implementations can also include the use of other types of particles or labels, either in addition to or instead of fluorescently labeled particles. For example in some cases captured cells can be stained with particles labeled with non-fluorescing dyes (e.g., dyes that exhibit a particular color in the visible spectrum) or directly with the dyes themselves without the use of additional particles. The use of combinations of fluorescently labeled particles and non-fluorescing particles is also possible, depending on the implementation.

The disclosed systems and techniques can be used for rare cell enrichment from native biological samples (e.g., whole blood, urine, spinal fluid). System 100 can be used as a sample preprocessor for molecular analysis systems, for example, used for gene sequencing. In some applications, the techniques can be used to characterize ascites tumor cells (ATCs) and monitoring of treatment of ovarian cancer without invasive surgical biopsies.

EXAMPLES

The methods and systems described herein are further illustrated using the following examples, which do not limit the scope of the claims.

Example 1—Arrays of Magnets

Figure 13A:
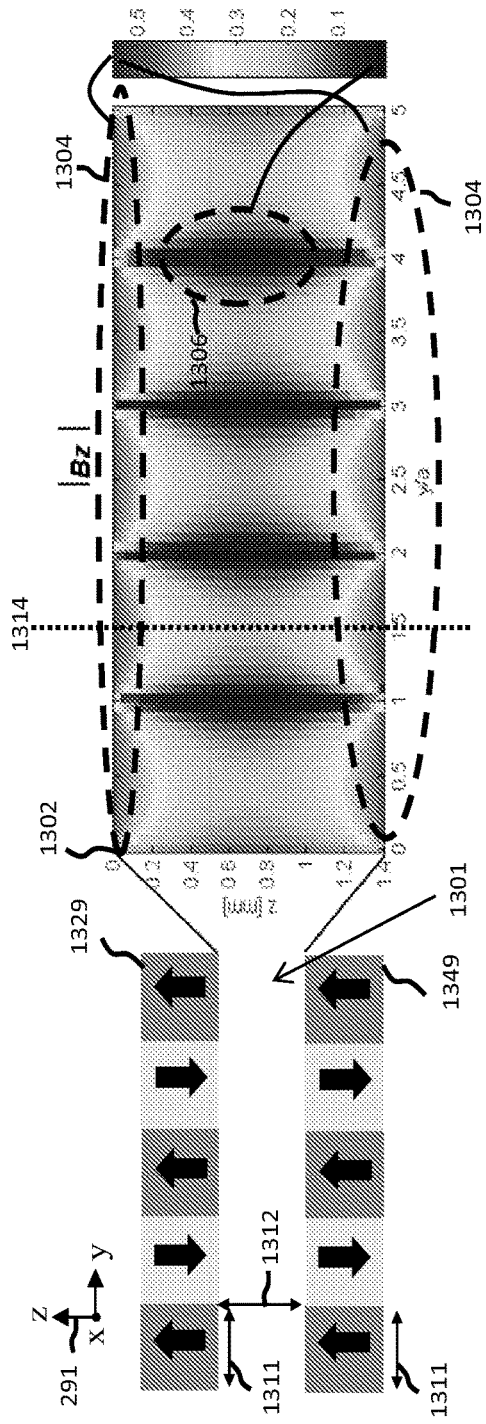
FIGS. 13A and 13B are schematic diagrams showing two configurations of arrays of magnets and their calculated magnetic field distribution.
Figure 13B:
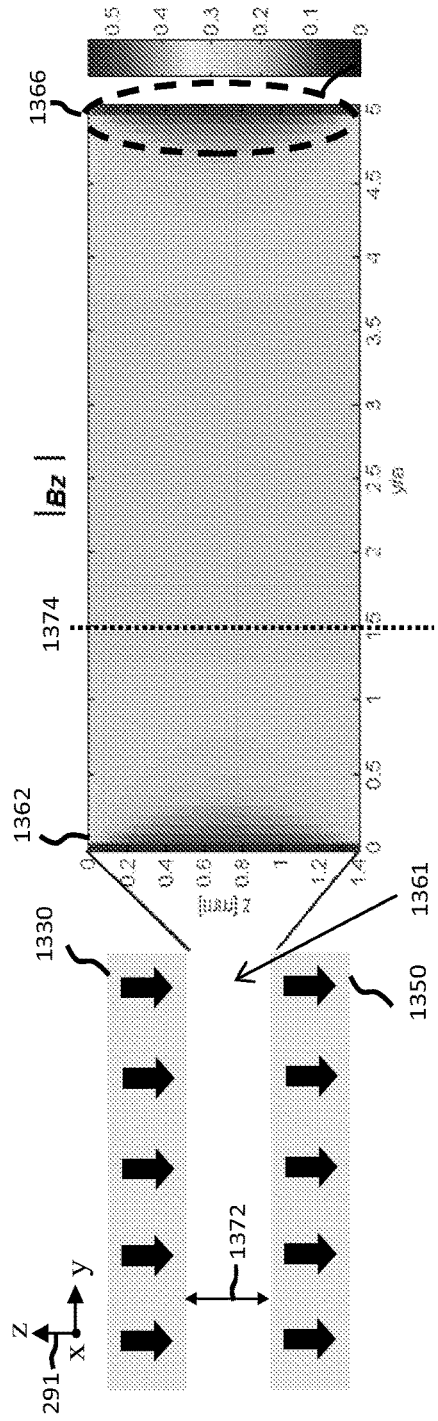

FIGS. 13A and 13B are schematic diagrams showing two configurations of 5×5 array of magnets and their calculated magnetic field distribution. The magnets were modeled to be made from NdFeB material with a saturation magnetization M=750 kA/m. Referring to FIG. 13A, 5×5 arrays 1329 and 1349 are arranged according to coordinate 291. Each magnet of the arrays 1349 and 1349 has a length 1311 of 1 mm. Hence, magnetic dipole moments alternate with a period of 2 mm in the y-direction. The closest surfaces between the arrays 1329 and 1349 have a separation distance 1312 of 1.4 mm. Image 1302 shows the calculated absolute value of magnetic field component in the z-direction (|Bz|) for region 1301 between the arrays 1329 and 1349. z=0 mm corresponds to the bottom surface of array 1329 and z=1.4 mm correspond to the top surface of array 1349. Regions 1304 have a large absolute value of magnetic field component in the z-direction (|Bz|) of about 0.48, while region 1306 has a small absolute value of magnetic field component in the z-direction (|Bz|) around 0.

FIG. 13B depicts 5×5 arrays 1330 and 1350 with a separation distance 1372 of 1.4 mm. In contrast to FIG. 13A, magnets of arrays 1330 and 1350 have their magnetic dipole moments pointing in the same direction without an alternating arrangement. Image 1362 shows the calculated absolute value of magnetic field component in the z-direction (|Bz|) for region 1361 between the arrays 1330 and 1350. z=0 mm corresponds to the bottom surface of array 1330 and z=1.4 mm correspond to the top surface of array 1350. Most of the region 1361 has absolute value of magnetic field component in the z-direction (|Bz|) of about 0.24 and is relatively uniform compared to the case of region 1301 in FIG. 13A. Region 1366 has a small absolute value of magnetic field component in the z-direction (|Bz|) around 0. Thus, comparing to FIG. 13A, the configuration shown in FIG. 13B, has a relatively uniform absolute value of magnetic field component in the z-direction (|Bz|) and with a smaller peak value.

Figure 14:
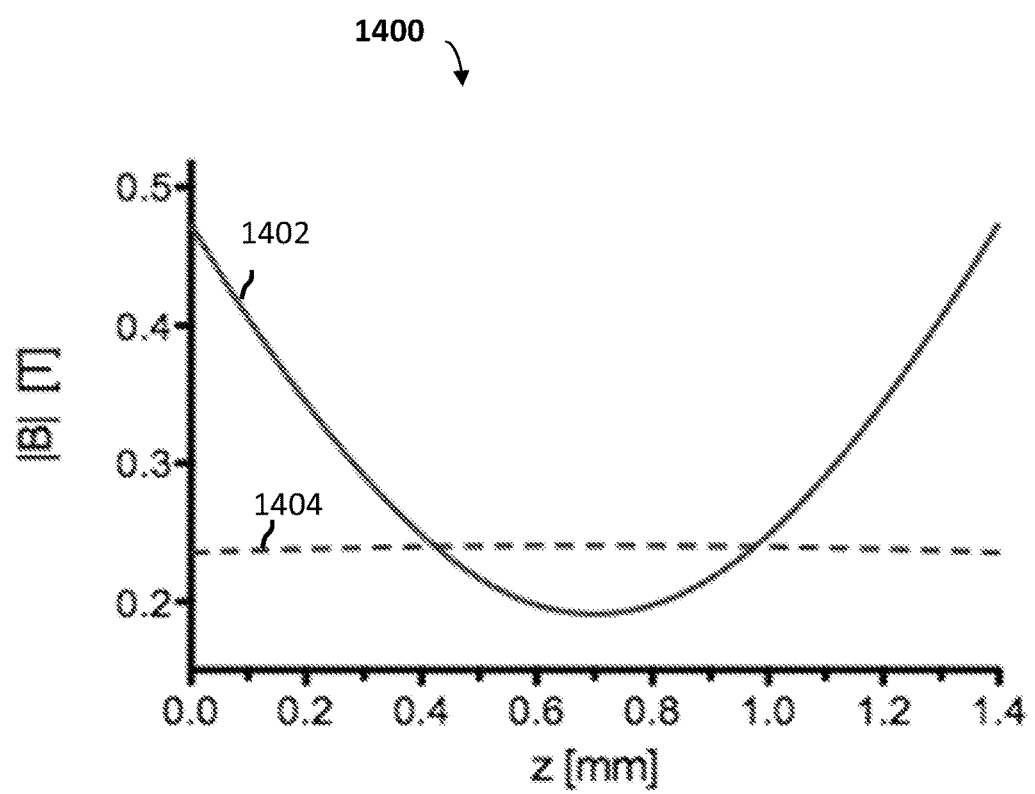
FIG. 14 is a plot depicting calculated magnitude of magnetic field ($|\vec{B}|$).

To compare the above two configurations, FIG. 14 is a plot 1400 presenting the calculated magnitude of magnetic field ($|\vec{B}|$) along cross-section lines 1314 and 1374 of FIGS. 13A and 13B. Solid curve 1402 is the magnitude of magnetic field ($|\vec{B}|$) along cross-section line 1314. Dashed curve 1404 is the magnitude of magnetic field ($|\vec{B}|$) along cross-section line 1374. The solid curve 1402 has an average magnitude of magnetic field ($|\vec{B}|$) of about 0.35 T. In some embodiments, the average magnitude of magnetic field ($|\vec{B}|$) of solid curve 1402 can be about 0.3 or more (e.g., between 0.3 T and 0.35 T, between 0.35 T and 0.4 T, between 0.45 T and 0.5 T). Moreover, the solid curve 1402 has a larger peak value of about 0.47 T and larger gradient than that of dashed curve 1404. Accordingly, the configuration of arrays 1329 and 1349 can provide a stronger magnetic force according to Eq. (1) than the configuration of arrays 1330 and 1350. In some embodiments, the peak magnitude value of solid curve 1402 can be about 0.45 or more (e.g., between 0.45 T and 0.5 T, between 0.5 T and 0.55 T, or between 0.55 T and 0.6 T).

Figure 15:
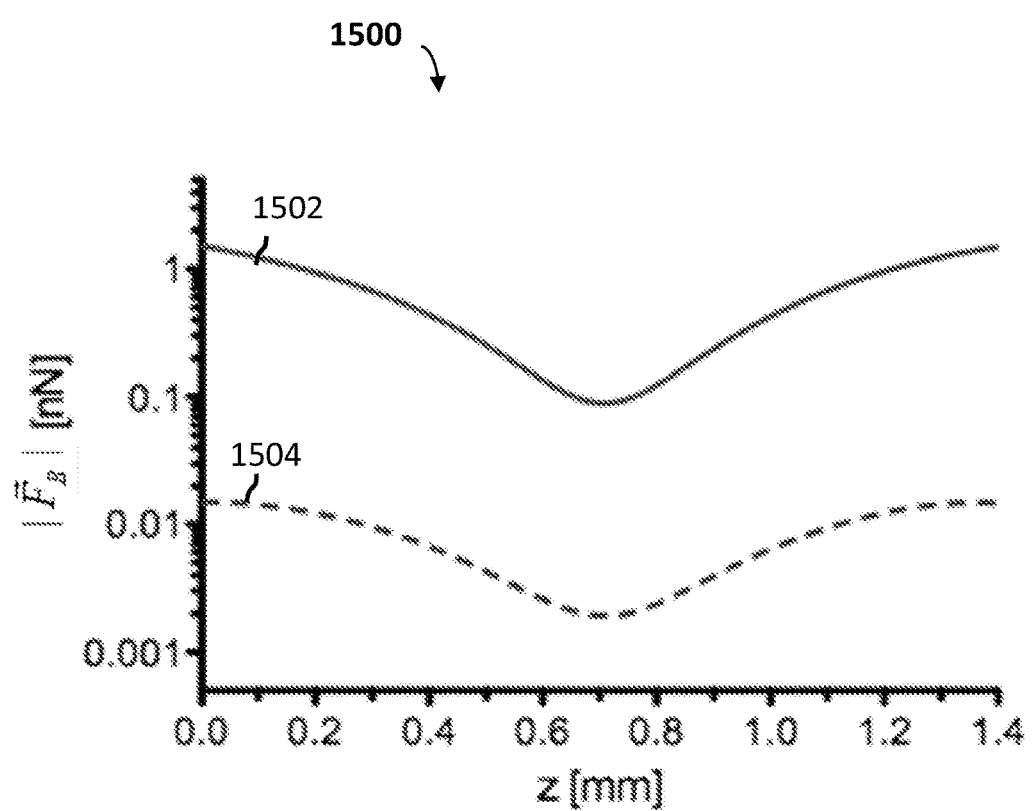
FIG. 15 is a plot depicting calculated magnitude of magnetic force $|\vec{F}_B|$ of a spherical particle.

FIG. 15 is a plot 1500 presenting the calculated magnitude of magnetic force $|\vec{F}_B|$ of a spherical particle with a 1 µm radius and susceptibility $\chi$=1 along cross-section lines 1314 and 1374. Solid curve 1502 is the calculated magnitude of magnetic force $|\vec{F}_B|$ along cross-section line 1314. Dashed curve 1504 is the calculated magnitude of magnetic force $|\vec{F}_B|$ along cross-section line 1374. As shown, the values of solid curve 1502 are about 100 times larger than that of dashed curve 1504. Accordingly, plot 1500 shows that the magnetic force in region 1301 between arrays 1329 and 1349 with alternating magnetic dipole moments can be significantly larger that the case of region 1361 between arrays 1330 and 1350.

Example 2—Testing of Particle Isolation

Figure 16:
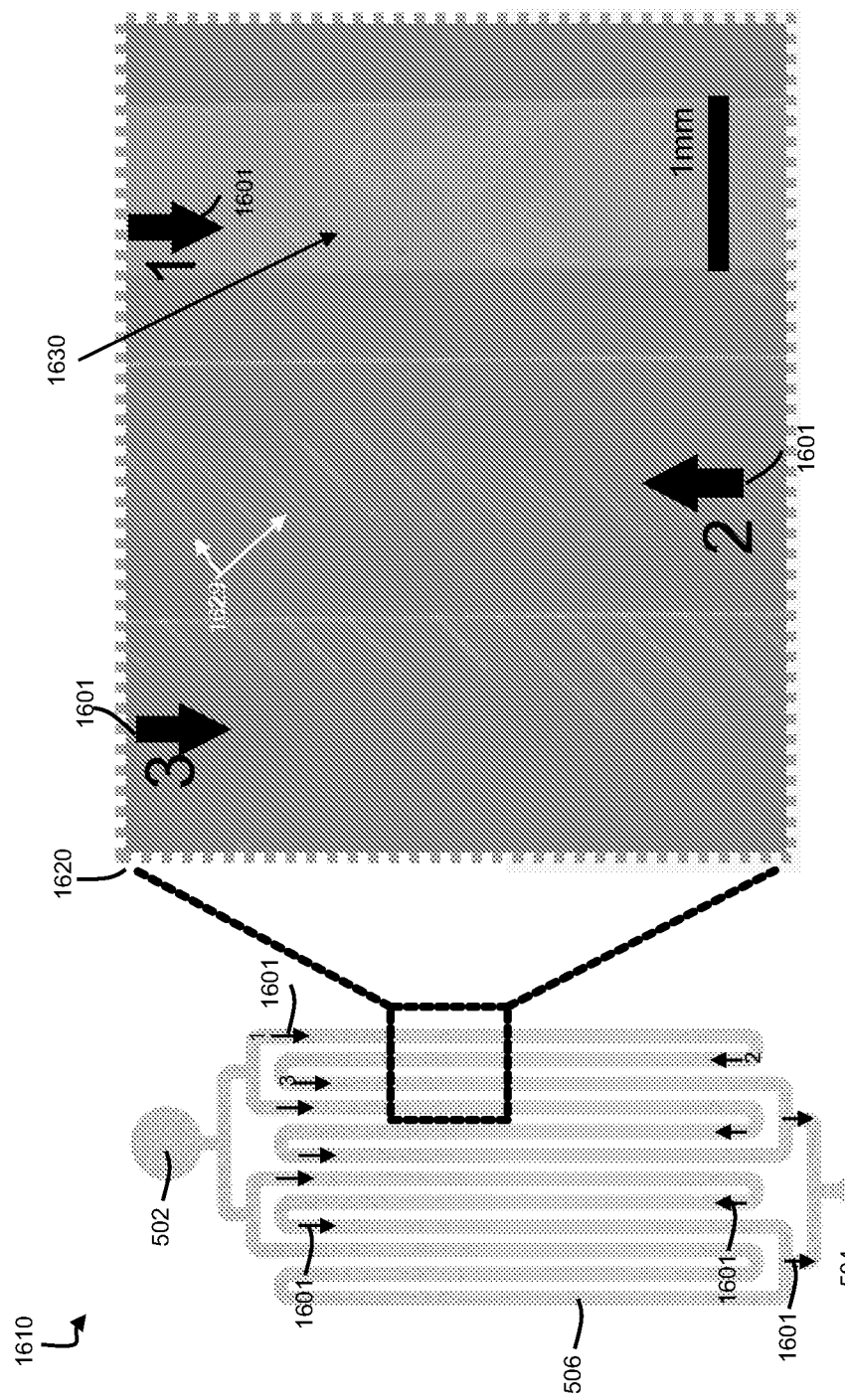
FIG. 16 is a schematic diagram of a portion of a microfluidic device used in a measurement.

To test the efficiency of arrays of magnets 102 and 104, an experiment was carried out to measure enrichment ratios depending of flow rates of a sample fluid. FIG. 16 is a schematic diagram of a portion of a microfluidic device 1610 used in the measurement. In a manner similarly described in relation to FIG. 5A, arrays of magnets 102 and 104 (not shown) sandwiched the channels 506, which had a width of about 1 mm. The sample fluid including non-magnetic particles 1629 and green magnetic particles 1630 were inserted into inlet 502. The sample fluid flowed through channels 506 along channel "1," "2" and "3" according to directions 1601. Image 1602 is a zoomed view of a region including channels labeled "1," "2" and "3." Most of the green magnetic particles 1630 were and attracted and stuck to walls of channel "1" by the magnetic fields provided by arrays of magnets 102 and 104. This result shows that the arrays of magnets 102 and 104 can be effective in capturing magnetic particles 1630 without the need of passing multiple windings of channel 506.

Figure 17:
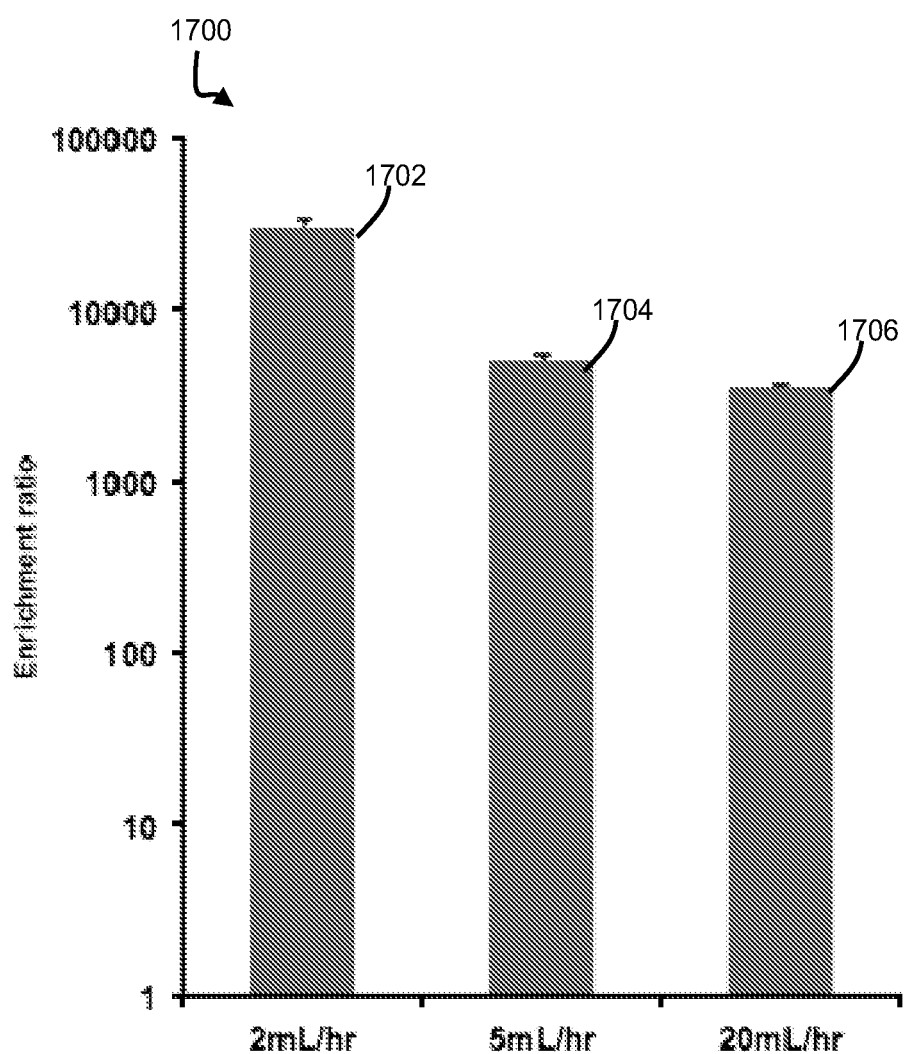
FIG. 17 is a plot depicting measurement results of enrichment ratios.

FIG. 17 is a plot 1700 showing measurement results of enrichment ratios relating to the number of non-magnetic particles 1629 and magnetic particles 1630 before and after passing through channel 506. The number of non-magnetic particles (P1) and the number of magnetic particles (M1) before passing the channels 506 were measured using a flow cytometer (LSRII, BD Biosciences). The number of non-magnetic particles (P2) and the number of magnetic particles (M2) after passing the channels 506 were also measured. The enrichment ratio was calculated according to:

$$\text{enrichment ratio} = \left(\frac{P2}{M2}\right) \bigg/ \left(\frac{P1}{M1}\right). \tag{2}$$

Bars 1702, 1704 and 1706 are the calculated enrichment ratio at flow rates of 2 mL/hr, 5 mL/hr and 20 mL/hr, respectively. In particular, the use of arrays of magnets 102 and 104 achieved a high enrichment ratio of about 3500 at a high flow rate of 20 mL/hr.

During the measurements, an image of inlet 502 showed a mixture of the non-magnetic particles 1629 and the green magnetic particles 1630. On the other hand, an image of outlet 504 showed only the non-magnetic particles 1629. These results demonstrated that a majority of the green magnetic particles 1630 were isolated by the arrays of magnets 102 and 104 and the non-magnetic particles 1629 dominantly reached the outlet 504.

Figure 18A:
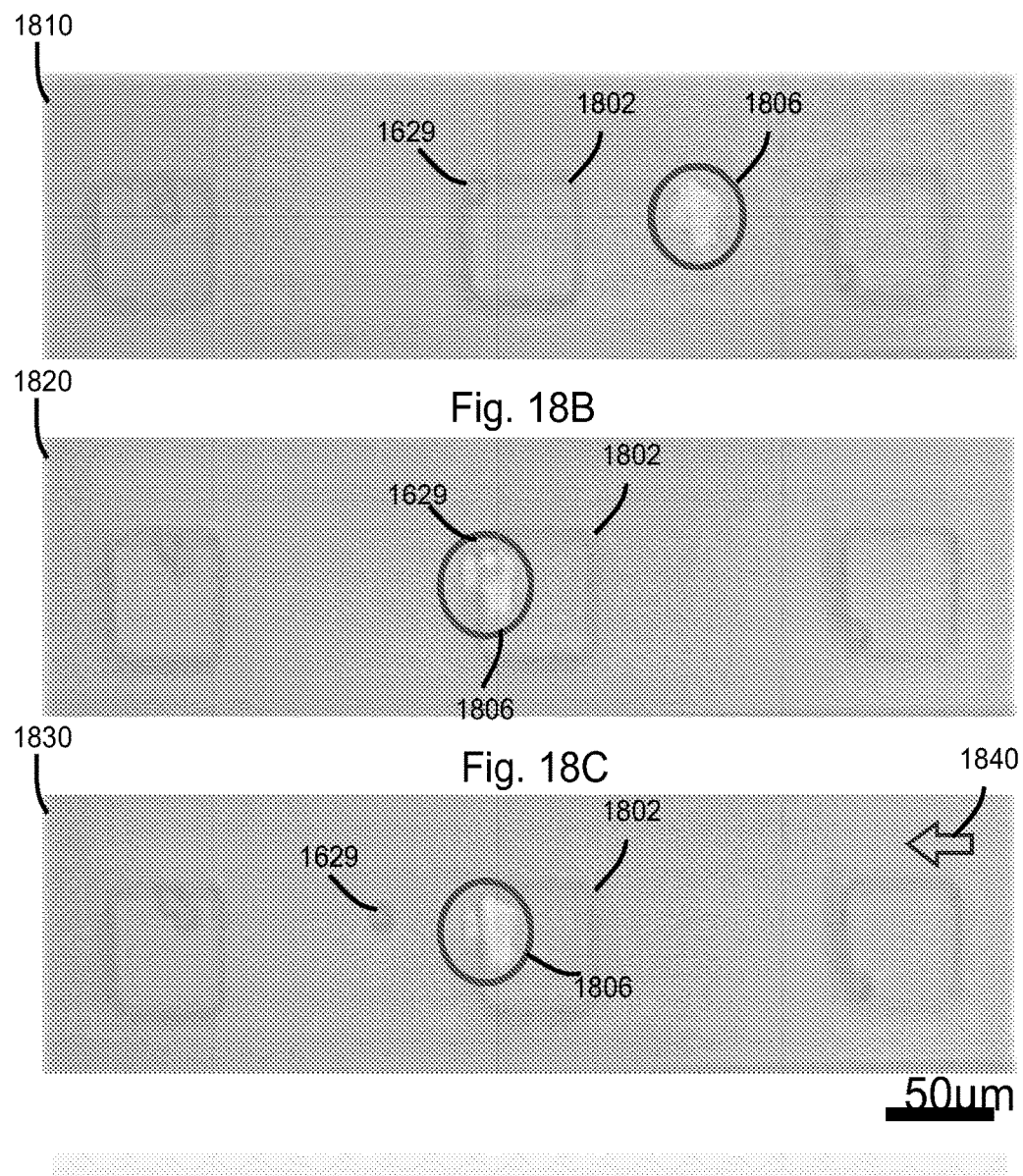

The experiment also demonstrated trapping and displacing a particle using an optical tweezer device. FIG. 18A is an image 1810 showing a particle capture site 1802 in the microfluidic device 1610. A single non-magnetic particle 1629 is captured in the particle capture site 1802. In this example, non-magnetic particle 1629 is not bound to a magnetic bead. The optical tweezer generated an optical trap 1806.

FIG. 18B is an image 1820 showing the optical trap 1806 trapping the non-magnetic particle 1829. By moving the focus position of the optical trap 1806 in a direction out of the drawing plane, the trapped non-magnetic particle 1629 was lifted upwards of the particle capture site 1802. Then the optical trap 1806 released the lifted non-magnetic particle 1829. FIG. 18C is an image 1830 showing the release non-magnetic particle 1629 being displaced by fluid flowing in direction 1840. The results demonstrated that the optical tweezer could manipulate and release a selected particle trapped in a particle capture site.

Figure 19:
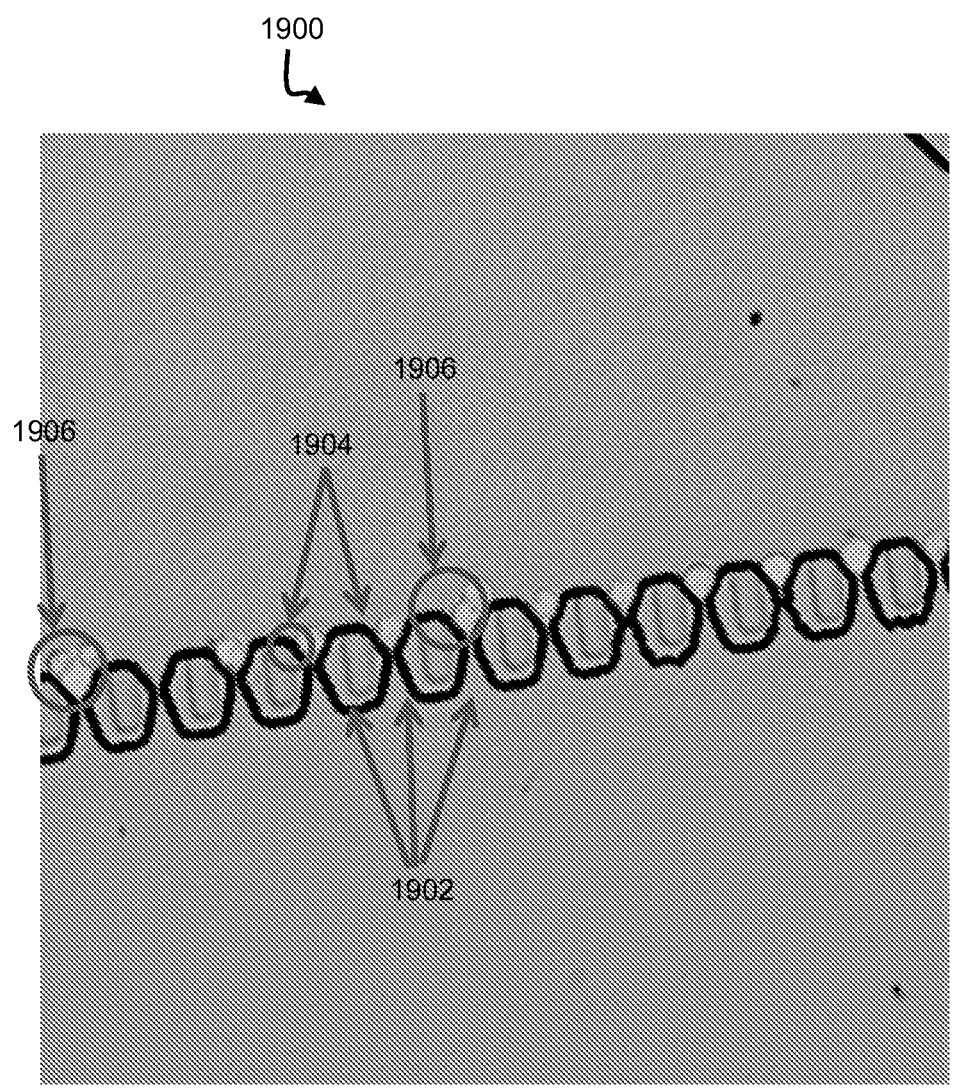
FIG. 19 is an image showing an example of a particle capture zone.

FIG. 19 is an image 1900 showing a particle capture zone of another experiment. In this experiment, following a depletion of host blood cells, target cancer cells were captured at the particle capture zone. The pink circular shapes of regions 1904 and 1906 were stained target cancer cells. A plurality of particle capture sites 1902 was designed to trap cancer cell of 5 μm or more in diameter. The particle capture sites 1902 had underpass-gaps at the middle of capturing sites to enhance capturing efficiency and remove red blood cells. Region 1904 corresponds to particle capture sites 1902 which captured single cancer cells. Region 1906 corresponds to particle capture sites 1902 which captured two or more cancer cells. As shown in image 1900, the particle capture sites 1902 had higher probability of capturing a single cancer cell than multiple cancer cells.

Example 3—Lymphoma Detection

Implementations of the system 100 can be used for a variety of experimental and clinical applications. To demonstrate one example of an application, an experiment was carried out to investigate cerebral nervous system (CNS) lymphoma in cerebrospinal fluid.

A microfluidic device 110 was fabricated to meet several exemplary criteria for processing CSF samples, including 1) a large number (e.g., >20,000) of cell capture sites to increase the likelihood of identifying monoclonal population when lymphoma cells make up as few as 0.1% of the total cells; 2) antibody-free and sized-based capture structure for cells in the 8-12 μm size range; and 3) pass-through gaps to remove erythrocytes.

Device Fabrication

Figure 20:
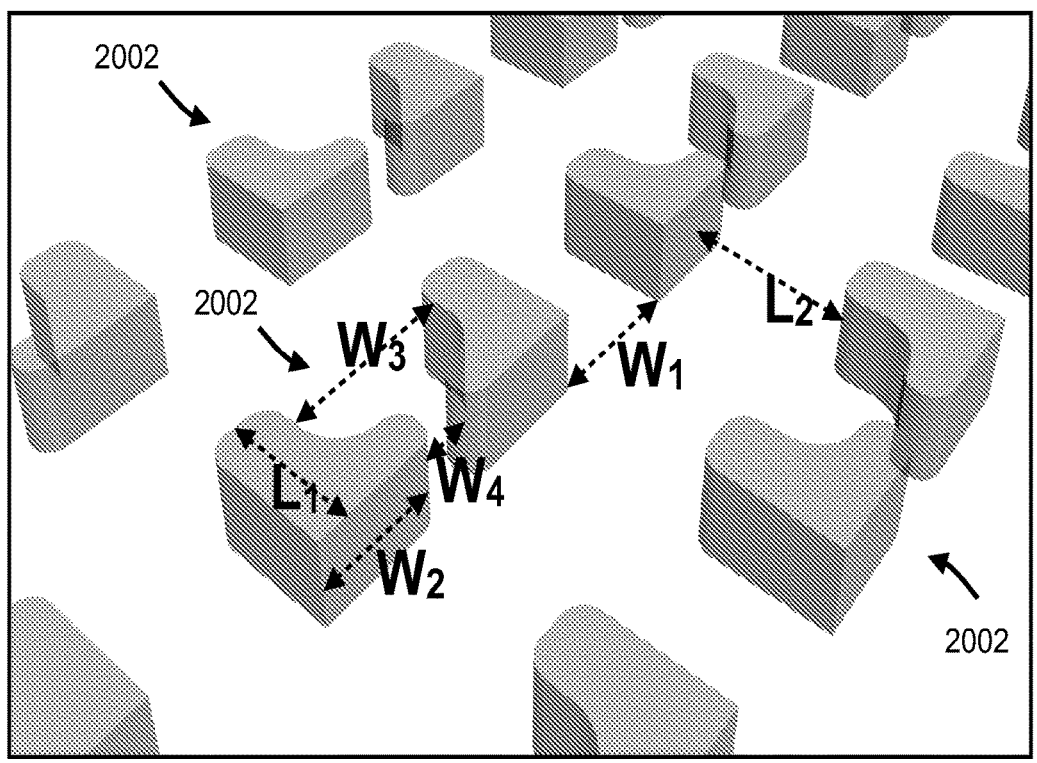
FIG. 20 is a schematic diagram illustrating a portion of an example of a capture zone.

In this experiment, the 2×4 cm² microfluidic device contained 24,000 staggered, butterfly-shaped traps arranged in four bands of 20×300. The fluidic system had a single-layer structure that is composed of a capture site region, a fluidic channel, and a debris filter at the inlet. Injected fluids (e.g. cells, buffers, antibodies) first pass through the microfilter array (200 μm in diameter) in order to filter large aggregates and debris. The fluids then passed through the capture site region (12000 μm in width; 5800 μm in length). FIG. 20 shows the detailed dimensions of the single-cell capture sites 2002, which were designed to capture lymphocytes ~10 μm in diameter. The microfluidic device includes two capture zone with different gap sizes (W1=30 μm and 16 μm; L2=40 μm and 25 μm) for enhancing the capture rate. The height of the fluidic channel is 25 μm.

The capture site architecture was optimized to trap a single lymphocyte, while a 4-μm gap between the butterfly "wings" was incorporated to allow smaller cells, such as erythrocytes, to pass through without being captured. The microfluidic devices were fabricated via standard soft lithography. In brief, an epoxy-based photoresist (SU-8 2025, MicroChem) was used to pattern a microfluidic channel on a silicon wafer. The wafer was then treated with trichlorosilane (Sigma Aldrich) under vacuum (1 hour). Polydimethylsiloxane (PDMS, Dow Corning) pre-polymer was mixed with a curing agent at a ratio of 10:1 (w/w), degassed under vacuum, and poured over the channel mold. The polymer was then cured on a hotplate (60° C., 1 hour). The cured PDMS structure was then peeled off, treated with $O_2$ plasma, and irreversibly bonded to a glass slide. Before use, each device was flushed with pluoronic copolymer solution (0.02 wt % F127 in water).

Sample Preparation

The cells used in this experiment were acquired from the following sources: DB, Toledo (Dr. Anthony Letai, Dana Farber Cancer Institute); RC-K8 (Dr. Thomas Gilmore, Boston University); SuDHL4, DOHH-2, Rec-1 (Dr. Russell Ryan, Massachusetts General Hospital); Daudi, Hut-78, Jurkat (ATCC). All cell lines (except Hut-78) were cultured (37° C. and 5% $CO_2$) in RPMI 1640 media (Invitrogen) supplemented with 10% fetal bovine serum (FBS). Hut-78 cell line was cultured (37° C. and 5% $CO_2$) in Iscove's Modified Dulbecco's Medium (Invitrogen) supplemented with 10% FBS.

The cells were titrated in this experiment as follows. Approximately $1.5 \times 10^6$ cells from culture flasks were washed with PBS and stained for 30 min at room temperature in 1.5 μg/mL Hoechst 33342 (Invitrogen) and APC anti-human-CD45 antibody according to manufacturer instructions (Clone HI30, BioLegend) in PBS containing 2% bovine serum albumin (BSA; Sigma Aldrich). Following a quick wash with PBS, cells were fixed in 2.6% paraformaldehyde (PFA) in PBS at room temperature for 20 min. Cells were then triple washed with PBS and counted using a hemocytometer (Hausser Scientific). The samples were diluted into quadruplicate aliquots of 10, 100, and 1,000 cells in 1 mL PBS in siliconized microtubes (Clear-view Snap-Cap, Sigma-Aldrich). Each sample was then introduced to a preconditioned device at a flow rate of 2 mL/hr. The captured cells were then counted via microscopy.

Prior to processing by the system 100, each sample for prepared for immuno-magnetic separation. In particular, given a sample of 5 mL, 5 mL PBS+4% BSA were added to each sample for final 2% BSA blocking at room temperature for 30 min. 5 mL were removed from each sample, and 25 uL of anti-CD3-biotin (0.5 mg/mL, BioLegend 344820) were added per sample, and incubated for 60 minutes at 4° C. 100 uL streptavidin coated magnetic beads were then added per sample, and incubated for 30 minutes at room temperature. 25 uL of anti-CD19-PE (BioLegend) were added to each sample, and incubated for 30 minutes at room temperature.

Experimental Methods

First, samples of cerebrospinal fluid were harvested, typically in the range of 1-3 mL. The collected samples were prepared for immune-magnetic separation (as described above), and immuno-magnetically separated using the system 100 in order to "pre-enrich" the sample prior to analysis, such that the relative abundance of lymphoma cells was increased. Each sample was loaded onto the microfluidic device for immune-magnetic separation, whereby cells expressing CD3 (a T-cell marker) were magnetically separated from cells that did not express CD3.

After separation, the remaining cells were captured in sub-nanoliter traps on the microfluidic device and stained within the microfluidic device for fluorescent imaging. Acquired images were then analyzed with an automatic computational technique to generate cell characterization data.

Staining on the microfluidic device was performed as follows. About 1000 DB, Daudi, or a 1:1 mixture of cells were diluted into 1 mL of artificial cerebrospinal perfusion fluid (aCSF; Harvard Apparatus). Samples were introduced to the device at the flow rate of 2 mL/hr. Following the cell capture, fix/perm buffer was perfused over the cells for 10 min, followed by permSB for 5 min, and PBS containing 2%

FBS and 1% BSA for 5 min, all at a flow rate of 1 mL/hr. A cocktail of antibodies containing 1 μL of anti-Ki-67, anti-CD19, and anti-CD20, and 2 μL of anti-κ light chain and anti-λ light chain was perfused over the cells at 1 mL/hr for 5 min. Lastly, to reduce background signal from antibodies binding to the channel surface, washing buffer (PBS with 2% FBS and 1% BSA) was perfused at 1 mL/hr for 5 min. Alternatively, cells were exposed to Ibrutinib-BFL using conditions recently described, followed by staining with Hoechst 33342 and anti-CD20-APC (clone 2H7; BioLegend). Images were captured on a Nikon Eclipse TE2000S inverted microscope (Nikon) equipped with four filter sets (#31000v2, #41001, #41002b, #41024; Chroma Technology).

Image analysis was performed as follows. Images were analyzed using an in-house Matlab (Mathworks) script. Briefly, images from the CD19/20 (PE) channel were thresholded and binarized using Otsu's method. Following thresholding, image regions were analyzed and filtered by eliminating any regions greater or less then preset total pixel areas based on the magnification of the images. Additional noise was filtered using "open-close" morphological filtering. Boundaries of the remaining regions were then recorded and overlaid on target channels where values for the pixels in each mask area for both lambda (Alexa Fluor 647) and kappa (Brilliant Violet 421) channels were generated. Final values for both lambda and kappa channels for each cell were calculated by averaging the most intense 25% of pixels in each region.

As the microfluidic device contains a large number of capturing sites, the microfluidic device allows for high-throughput analysis. For instance, with typical flow rates of 2-5 mL/hr, target cells could be captured and stained in <1 hour, which may be of particular importance for processing clinical samples.

The performance of the microfluidic device for cell capture was characterized. DB GCB-type DLBCL (diffuse large B-cell lymphoma) and the Daudi Burkitt lymphoma cell lines were stained for CD45 (an extracellular pan-lymphocyte marker) and nucleus, and samples were prepared with the nominal cell counts of 10,100, or 1000 of the DB or Daudi cells. When these samples were processed by the microfluidic device, the observed capture efficiency was >90%; this contrasts with the 17-30% cell loss that occurs at each centrifugation step in traditional sample processing.

Fluorescent 10-μm microbeads (Bangs Laboratory) were used to test capture efficiency and to find the optimal flow rate. The bead solution was diluted to a concentration of 3000 beads/mL, and an estimated 300 beads were introduced to the device. Using a syringe pump, we applied negative pressure at the channel outlet to generate fluidic flow. The number of captured beads was counted via florescence microscopy. The optimal flow rate for maximal capture yield was determined to be between 2-5 mL/hr. At lower flow rates, cells could have more time to follow the fluidic stream, thereby bypassing capture sites.

Captured cells were analyzed on the microfluidic device through multi-color immuno-microscopy. Three classifications were performed: 1) the use of CD19 and/or CD20 to determine B cells; 2) the use of kappa or lambda light chains to identify clonal populations; and 3) additional phenotypic markers for subtyping and prognostic tasks. These markers and their respective antibodies were validated by profiling a panel of cell lines via flow cytometry. Besides the B-cell lymphoma lines Daudi and DB, SuDHL4, DOHH2, and Toledo GCB-type DLBCL lines, the RC-K8 ABC-type DLBCL line, and the Rec-1 mantle cell lymphoma line were also profiled. Hut-78, a T-cell line, was used as a control.

Results

The profiling results showed the importance of including both CD19 and CD20 to identify B cells; not all B-cell lines were found to express both markers. This finding is also supported by other reports that showed decreased CD20 in lymphomas either due to the cancer cell-of-origin or anti-CD20 immunotherapy. The assay also showed the restricted expression of kappa or lambda light chain surface immunoglobulins, which are markers of clonality, across the cell lines.

Several different lymphomas arise from germinal center B cells, such as Burkitt and some DLBCLs (GCB-type), but most primary CNS lymphomas are ABC-type DLBCLs. As expected, we found that the GCB marker CD10 is expressed in all the GCB cell lines tested, but not in ABC-type or mantle cell lymphoma. Since ABC-DLBCLs tend to be more aggressive, we chose Ki-67 as an important marker for characterization and prognosis. Our data for the DB, DOHH2, and Rec-1 lines suggests that low Ki-67 in a monoclonal population would indicate the need to test additional lymphoma markers, such as for GCB-type DLBCL or mantle cell lymphoma. MUM1 may also be important, as it was shown to be expressed in over 90% of PCNSLs.

Figure 21A:
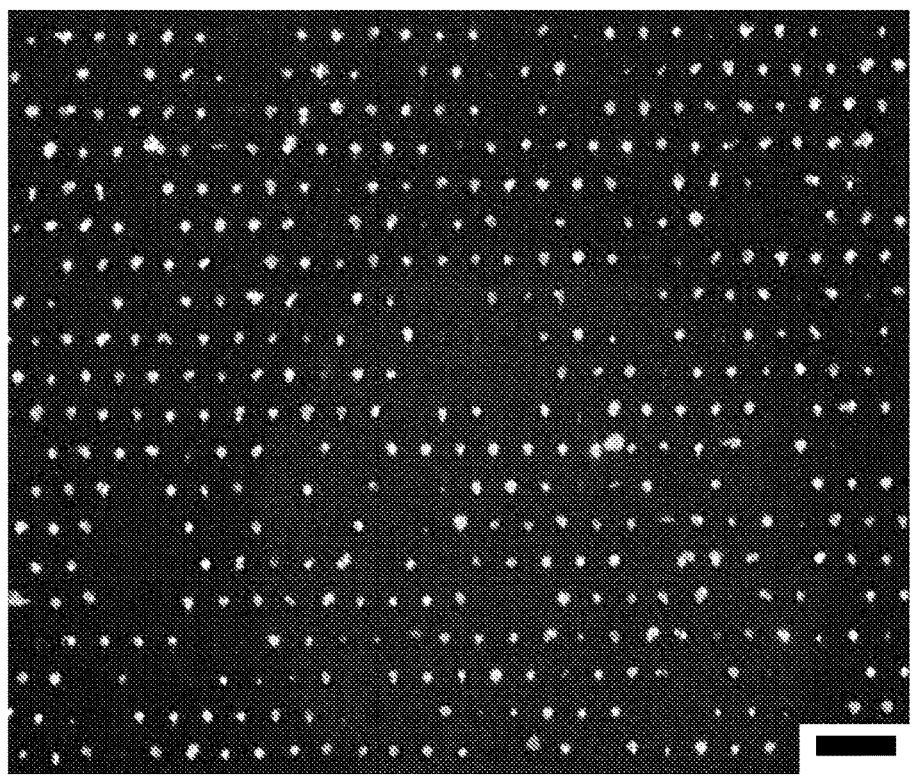
FIG. 21A is an image showing an overlay of four imaging channels after a mixture of DB cells (a B lymphoblast cell line) and Daudi cells (a B lymphoblast cell line) was captured and stained on a microfluidic device.
Figure 21B:
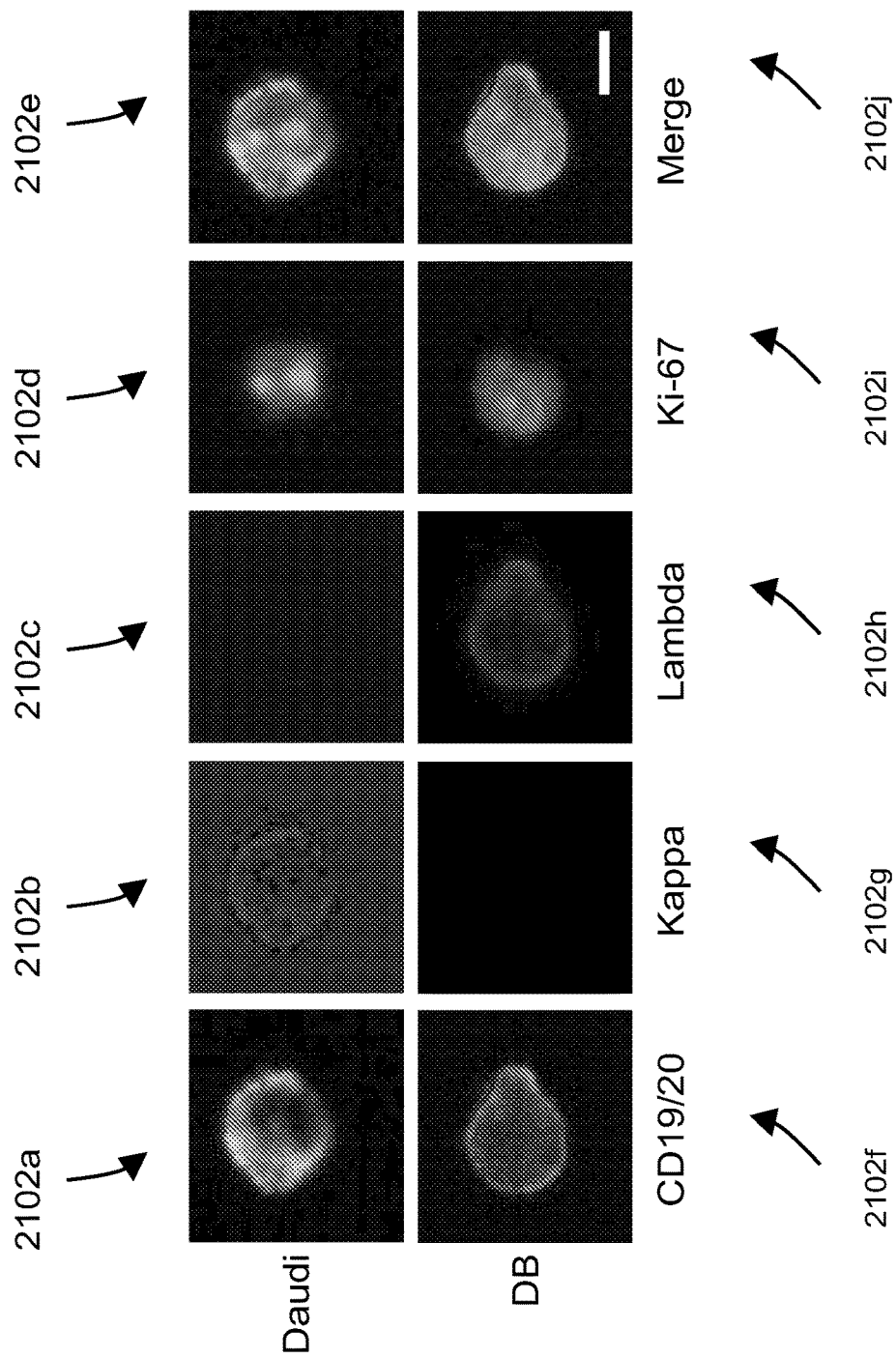
FIG. 21B is an image showing selected portions of the overlay shown in FIG. 21A.

Daudi and DB cells were used as a model system for analysis on the microfluidic device, since they respectively highly express kappa and lambda light chain. To demonstrate both extracellular and intracellular antigen analysis, we performed staining of CD19/CD20, kappa/lambda, and Ki-67 on the microfluidic device. We prepared cells for testing on the micro fluidic device by diluting DB and Daudi lymphoma cells into artificial CSF. The cells were then fixed and stained on the microfluidic device, and imaged in four channels. FIG. 21A shows an overlay 2100 of the four imaging channels after a 1:1 mixture of DB and Daudi cells was captured and stained on the microfluidic device. As shown in FIG. 21A, some cell capture sites 2104 exhibit fluorescence, while others do not. As several cell capture sites 2104 are shown in a single image, the cells contained in each of these cell capture sites 2104 can be analyzed from a single image. FIG. 21B shows two selected portions of the overlay 2100 (a first portion shown in the row of images 2106a, and a second portion shown in the row of images 2106b). Row 2106a corresponds to a first capture site containing a Daudi cell, and each of the images 2102a-e of row 2106a shows the first capture site according to different fluorescent channels. Row 2106b corresponds to a second capture site containing a DB cell, and each of the images 2102f-j of row 2106b shows the second capture site according to the different fluorescent channels. In observing the presence or absence of certain types of fluorescence, one can identify differences in the expression of particle biomarkers between the cells. For example, as shown in images 2102b-c, the Daudi cell captured in the first capture site expresses kappa, but does not express lambda. In contrast, as shown images 2102g-h, the DB cell captured in the second capture site does not express kappa, but expresses lambda. Thus, this experiment demonstrates that that high-resolution imaging can be performed for individual cells and their markers. Further, the experimental also demonstrates that although the cell populations appear to be heterogeneous, their restricted kappa/lambda expression can be seen at higher magnification.

Figure 22A:
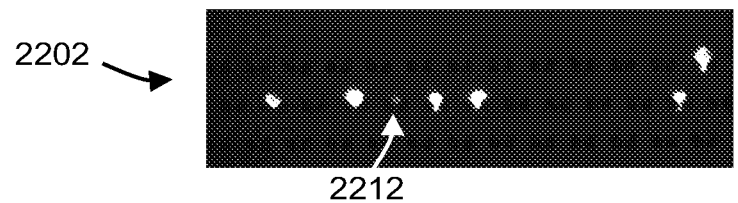
FIG. 22A is an image depicting the intensity of light within the phycoerythrin (PE) channel for a portion of a capture region.
Figure 22B:
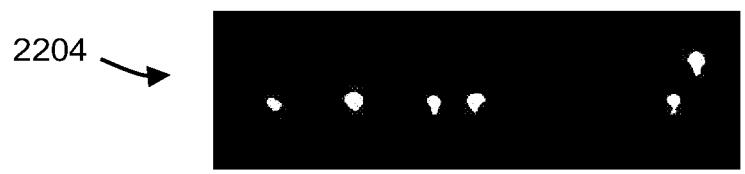
FIG. 22B is an image that results after performing an intensity-based thresholding on the image shown in FIG. 22A.
Figure 22C:
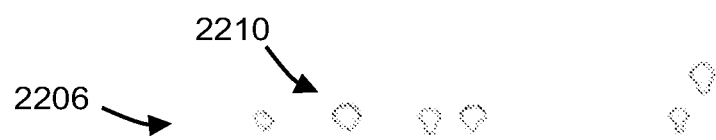
FIG. 22C is an image showing masks that are generated based on the image shown in FIG. 22B.
Figure 22D:
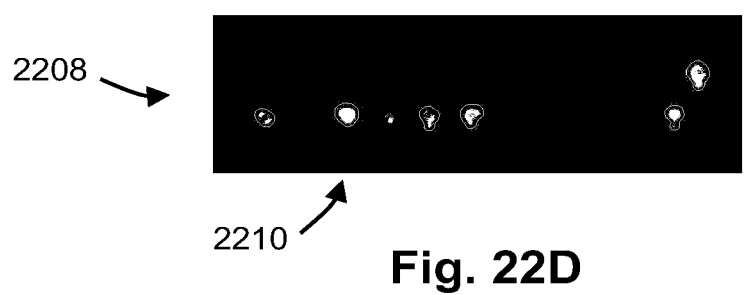
FIG. 22D is an image showing the application of the masks shown in FIG. 22C to additional images.

As a proof-of-concept of lymphocyte analysis from clinical samples, we developed an image-processing technique for clonality assessment. Following the staining of cells, we first made a mask around cells expressing CD19 and/or CD20, and then quantified the mean fluorescence intensity from our target channels in each individual cell. The mask was generated by performing intensity-based thresholding on each image, and filtering the thresholded image to obtain binary masks. For example, FIG. 22A shows an image 2202 that depicts the intensity of light within the PE channel for a portion of the particle capture zone. FIG. 22B shows an image 2204 that results after performing an intensity-based thresholding on the image 2202 (e.g., where pixels greater than or equal a particular intensity are identified as exhibiting fluorescence, while pixels less than that particular intensity are identified as not exhibiting fluorescence). FIG. 22C shows an image 2206 of the resulting masks 2210 that are generated based on the thresholded image 2204. As shown in FIG. 22D, each of the generated masks 2210 were used to analyze additional images 2208 that depicts the intensity of light within a different color channel (e.g., color channels associated with other fluorophores, such as Alexa Fluor 647 and Brilliant Violet 421). A size filter was also included to exclude non-cell debris from analysis (e.g., debris 2212 shown in FIG. 22A).

As the masks 2210 were created based on the fluorescence associated with CD 19 and/or CD20, the mask corresponds to the location of cells expressing CD19 and/or CD20 (e.g., lymphocyte cells). Thus, the mask can be used to identify specific portions of the image known to contain lymphocytes. These masks can be applied to other images (e.g., images depicting fluorescent associated with Alexa Fluor 647 and Brilliant Violet 421 fluorescence to determine if the lymphocytes in those regains are lambda or kappa-expressing cells.

Figure 23:
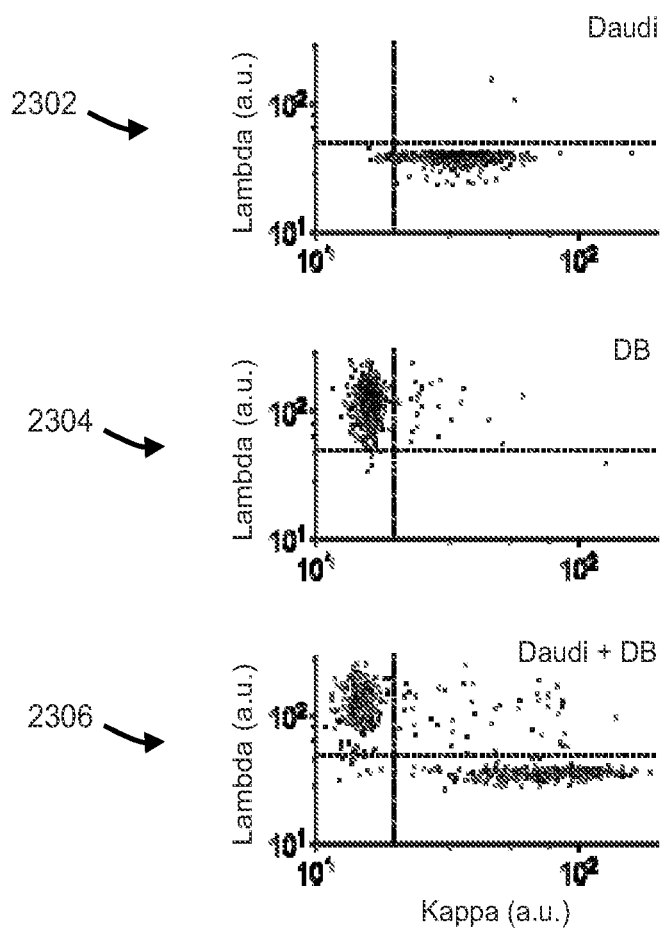
FIG. 23 is a collection of plots depicting the distribution of masked regions of images of a capture zone on the basis of a first intensity (lambda, λ) and a second intensity (kappa, κ) for different cells.
Figure 24:
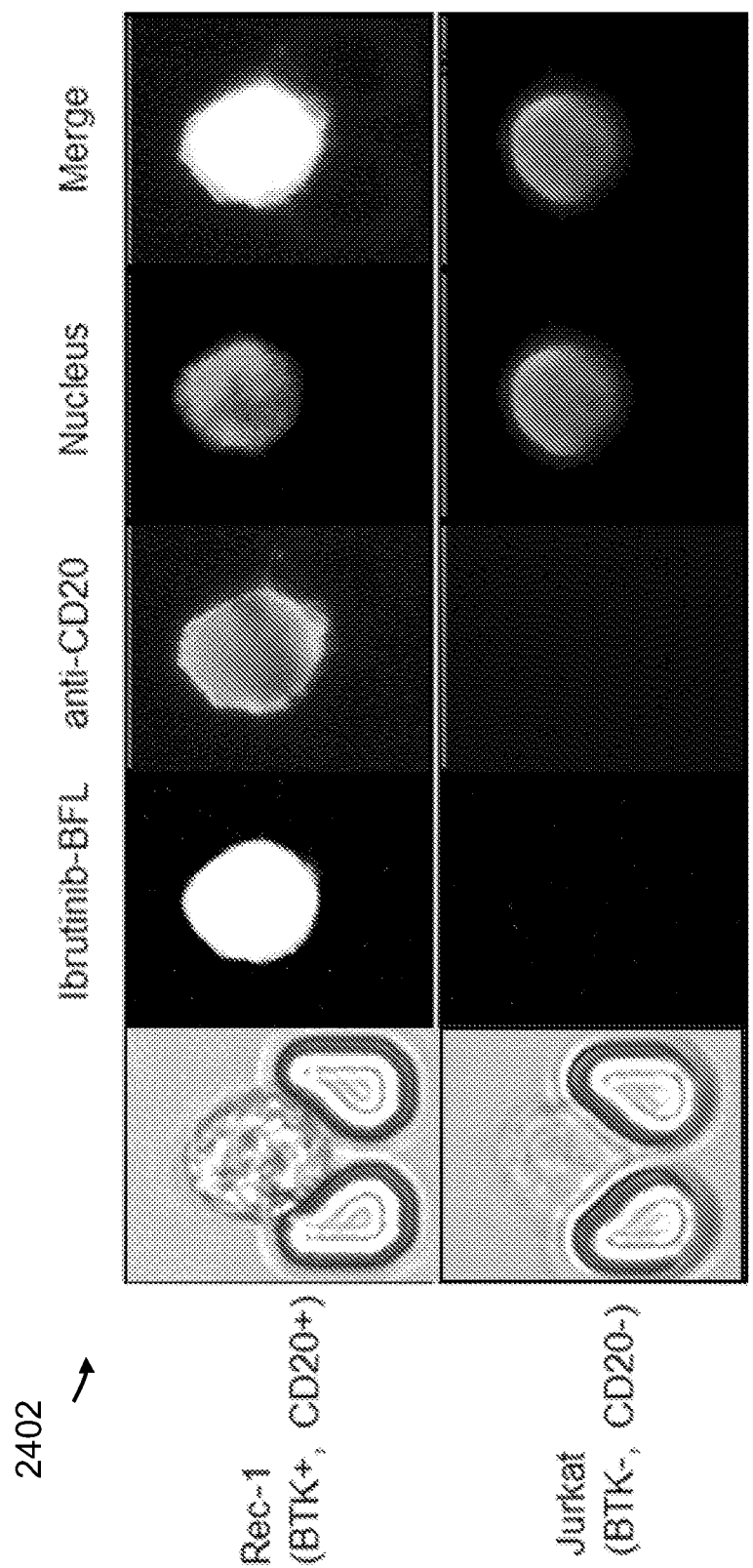
FIG. 24 is an image depicting fluorescently labeled Rec-1 cells and Jurkat cells.

FIG. 23 shows plots 2302, 2304, and 2306 depicting the distribution of masked regions of images of the capture zone on the basis of their Alexa Fluor 647 intensity (lambda) and Brilliant Violet 421 intensity (kappa), analyzed according to the masked regions 2210. As shown in FIG. 23, after quantification, we were able to distinguish DB (lambda-expressing) cell populations (as shown in plot 2304) and Daudi (kappa-expressing) cell populations (as shown in plot 2302) from samples containing about 1,000 cells. The combined distribution for both of the cell populations are shown in plot 2306. Thus, we were able to differentiate between two different types of cells within the sample population. We further performed drug sensitivity testing that would be clinically useful to guide intrathecal and/or systemic chemo- and targeted therapies. We used a companion imaging drug that has recently been reported, Ibrutinib-BFL, which is an inhibitor of Bruton's Tyrosine Kinase (BTK); other imaging drugs include fluorescent rituximab or caged methotrexate. Ibrutinib is approved for several B-cell malignancies, including mantle cell lymphoma, and the Rec-1 cell line has been shown to be sensitive to the drug. FIG. 24 shows images 2402 of Rec-1 cells and Jurkat cells with Ibrutinib-BFL on the microfluidic device. As shown in FIG. 24, Rec-1 cells exhibit fluorescence when incubated with Ibrutinib-BFL, and similarly exhibit fluorescent when incubated with an anti-CD20 fluorescent marker. However, Jurkat cells do not exhibit fluorescent when incubated with either Ibrutinib-BFL or the anti-CD20. Thus, imaging the Rec-1 cells with Ibrutinib-BFL on the microfluidic device shows not only the binding of Ibrutinib, but also their cell-to-cell heterogeneity due to differences in BTK inhibitor sensitivity and BTK protein turnover. As such, this demonstrates that implementations of the system 100 can be used to differentiate between cell types (e.g., CD20 expressing cells vs. non-CD20 cells) as well as between cell types that are differently sensitive to certain types of drugs (e.g., Ibrutinib).

CNS lymphoma is often difficult to diagnose and characterize at the site of disease, in many cases requires multiple invasive lumbar punctures to retrieve sufficient numbers of cells to allow for cytopathologic analysis. This experiment demonstrates that the paucicellularity and heterogeneity of CSF samples can be overcome through implementations of the above described microfluidic system that enable characterization of populations of lymphoma cells in the CSF on a single-cell level. Here, we show that we can indeed image both intracellular and extracellular diagnostic markers from lymphoma cells spiked into artificial CSF in under an hour, and further use an image-processing algorithm to quantitate their expression level. By adding additional criteria, differential diagnosis using the Hans algorithm can identify the cell-of-origin of a PCNSL, perhaps pointing to an undiagnosed systemic lymphoma if germinal center origin is found. Thus, this experiment demonstrated that the system 100 can be used to analyze different types of cells on the basis of their intracellular and extracellular biomarkers, and demonstrated that this can be used to different between different types of disease cell subtypes. Further, this experiment also demonstrated that the system 100 can be used to examine time-dependent characteristics of one or more cell types.

For secondary CNS lymphoma, it is often important to know the extent of disease, its aggression, and its response to treatment. Methotrexate is currently used intrathecally or at very high systemic doses to treat CNS disease, but it has thus far not been possible to track response to treatment other than by low resolution MRI or insensitive cytology, neither of which would catch minimal disease. The system 100 enables profiling lymphoid cells in CSF based on kappa/lambda restriction or proliferative grade, or customizing antibody staining for intracellular or extracellular markers based on particular characteristics of the primary tumor (e.g. c-Myc rearrangement, CD10, CD5, etc.) in order to track CNS lymphoma cell counts c over time and to make prognostic assessments. Additionally, there are several new lymphoma drugs in clinical trials, yet few are tested for CNS efficacy. The system 100 can also provide a companion diagnostic that can directly test for brain-blood-barrier drug permeability or look for specific marker inhibition following intrathecal administration, such as BTK inhibitors or new generation anti-CD20 agents. For example, as demonstrate above, to test for such drug accumulation (single cell pharmacokinetics) in primary lymphoma cells, we tested Ibrutinib-BFL directly on a microfluidic device. Finally, the system 100 also allows for the removal of CSF after intrathecal injection of chemotherapy drugs to track treatment response over time.

Although the above described experiment demonstrates one application of the described implementations, this is merely an illustrative example. In practice, implementations can be used for different applications than those described above. Further, the techniques used in the experiment can be modified to suit the application at hand. As an example, in some cases, B cells can be further purified by negative selection of other cell types, such as T cells and monocytes. Since the capture is passive (e.g., no antibodies are used to capture cells within the capture zone of the microfluidic device), in some cases, we can also use tweezing techniques to remove single cells of interest off the microfluidic device for further characterization, such as by quantitative PCR and sequencing. In some cases, an imager or smartphone camera readout can be used to enable the microfluidic device to be used for lymphoma diagnosis in resource-poor settings. In some cases, a 1:5 cutoff ratio of kappa-to-lambda fluorescence signal would be enough to establish clonality with high specificity.

OTHER EMBODIMENTS

It is to be understood that while various implementations have been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A system for isolating particles comprising:
   a first array of magnets arranged in a two-dimensional checkerboard pattern of magnets with directly adjacent magnets in the array having dipole moments aligned in opposite directions;
   a second array of magnets arranged in a two-dimensional checkerboard pattern of magnets with directly adjacent magnets in the array having dipole moments aligned in opposite directions, wherein the second array of magnets is arranged generally in parallel with and spaced apart from the first array of magnets; and
   a microfluidic device comprising:
      a substrate;
      an inlet arranged on the substrate and configured to receive a fluid sample;
      an outlet arranged on the substrate;
      a first region of the substrate comprising a channel connected to the inlet, wherein the first region of the substrate is arranged to sandwich the channel between the first and second arrays of magnets; and
      a second region of the substrate in fluid communication with the channel and comprising a particle capture zone containing a plurality of particle capture sites, wherein each particle capture site comprises a receptacle sized to confine a first type of particle and an opening in fluid communication with the outlet, wherein a size of the receptacle is larger than a diameter of the first type of particle, and a size of the opening is smaller than the diameter of the first type of particle to trap the first type of particle in the receptacle, but allow passage of articles smaller than the opening.

2. The system of claim 1, wherein each of the magnets in the first array of magnets and the second array of magnets comprises NdFeB, SmCo, Fe, Ni, Co, FePt, MnFe2O4, CoFe2O4, NiFe2O4, ZnMnFe2O4, or iron oxide.

3. The system of claim 1, wherein a peak magnitude value of a magnetic field strength at a point between the first array of magnets and the second array of magnets is about 0.45 T or more.

4. The system of claim 1, wherein a magnitude of an average magnetic field strength along a line extending from the first array of magnets to the second array of magnets is about 0.35 T or more.

5. The system of claim 1, further comprising:
   a tweezer device configured to displace the particle captured in one of the particle capture sites; and
   a receiver device configured to receive the displaced particle,
   wherein the tweezer device is an optical tweezer device, and wherein the optical tweezer device comprises an optical source for generating an optical beam, and a lens for focusing the optical beam into one of the particle capture sites.

6. The system of claim 1, wherein, for at least one particle capture site, the receptacle is sized to receive and confine a single first type of particle, and
   wherein, for the at least one particle capture site, the opening is small enough to prohibit passage of the first type of particle and large enough to allow passage of a second type of particle.

7. The system of claim 1, wherein at least one particle capture site comprises a first wall and a corresponding second wall,
   wherein the receptacle is bounded by the first wall and the second wall, and
   wherein the opening is defined between an end of the first wall and an end of the second wall.

8. The system of claim 1, wherein at least one of the particle capture sites comprises a wall, wherein the receptacle is defined by a recess in the wall, and wherein the opening extends from the receptacle on a first side of the wall to a second opposite side of the wall.

9. The system of claim 1, further comprising a fluid manifold arranged on the substrate between the particle capture zone and the outlet.

10. A method for isolating particles, the method comprising:
    providing a first and a second array of magnets, wherein the first and second arrays of magnets are positioned to sandwich a region including a channel of a microfluidic device, and wherein the magnets in the first and second arrays are arranged in a two-dimensional checkerboard pattern of magnets with directly adjacent magnets in each array having dipole moments aligned in opposite directions;
    providing a sample fluid comprising a plurality of particles into the channel, wherein at least one first type of particle is bound to a magnetic bead, and wherein a magnetic field extending between the first and second magnet arrays within the channel causes the at least one first type of particle to separate from remaining particles in the fluid sample;
    providing the fluid sample containing the remaining particles to a particle capture zone of the microfluidic device, wherein the particle capture zone comprises a plurality of particle capture sites each comprising a receptacle that is larger than a diameter of a second type of particle in the remaining particles and that has an opening that is smaller than the diameter of the second type of particle to trap the second type of particle in the receptacle, but allow passage out of the receptacle of other remaining particles smaller than the opening; and
    capturing one or more of the second type of particles in the receptacles of the particle capture sites of the microfluidic device, wherein the one or more second type of particles are not bound to a magnetic bead.

11. The method of claim 10, wherein capturing the second type of particle comprises receiving a single second type of particle in a receptacle of one of the particle capture sites.

12. The method of claim 10, further comprising displacing the one or more second type of particles from the particle capture sites using an optical tweezer, wherein displacing the one or more second type of particles from the particle capture sites comprises displacing a single one of the second type of particles from a single one of the particle capture sites, and wherein the optical tweezer is configured to provide a plurality of optical traps.

13. The method of claim 10, further comprising flowing a first additional fluid through at least the particle capture zone, wherein the first additional fluid comprises a plurality of first fluorescent markers, and the method further comprises allowing the plurality of the first fluorescent markers to bind to one or more of the second type of particle.

14. The method of claim 13, further comprising:
optically exciting the first fluorescent markers bound to the one or more second type of particle;
obtaining an image of the one or more second type of particle; and
determining a characteristic of the second type of particle based on the obtained image.

15. The method of claim 14, wherein determining the characteristic of the second type of particle based on the obtained image comprises determining an intensity of fluorescence associated with the second type of particle based on the obtained image.

16. The method of claim 14, further comprising:
flowing an elutant through at least the particle capture zone, wherein flowing the elutant causes the fluorescently labeled particles to release from second type of particle;
flowing a second additional fluid sample through at least the particle capture zone, wherein the second additional fluid comprises a plurality of a second type of fluorescent marker, and wherein one of more of the second type of fluorescent markers bind to one or more of the second type of particle.

17. The method of claim 16, further comprising:
optically exciting one or more of the second fluorescent markers bound to second type of particle;
obtaining a second image of the second type of particle; and
determining a characteristic of the second type of particle based on the obtained second image, wherein the characteristic comprises a presence or absence of a second biomarker expressed by the second type of particle different than the first biomarker.

18. The method of claim 13, wherein the first additional fluid substance comprises a drug such that the second type of particle is exposed to the drug.

19. The method of claim 10, further comprising culturing the at least one second type of particle in the particle capture zone after the at least one second type of particle is captured.

* * * * *

UNITED STATES PATENT AND TRADEMARK OFFICE
CERTIFICATE OF CORRECTION

PATENT NO.         : 10,151,753 B2
APPLICATION NO.    : 15/104775
DATED              : December 11, 2018
INVENTOR(S)        : Hakho Lee et al.

It is certified that error appears in the above-identified patent and that said Letters Patent is hereby corrected as shown below:

In the Claims

Claim 1, Line 47:
Delete "articles" and insert --particles--

Signed and Sealed this
Nineteenth Day of February, 2019

Andrei Iancu
*Director of the United States Patent and Trademark Office*